US012636329B2

(12) United States Patent
Wu

(10) Patent No.: US 12,636,329 B2
(45) Date of Patent: May 26, 2026

(54) RECOMBINANT ONCOLYTIC VIRUS, PREPARATION METHOD THEREFOR, USE THEREOF AND MEDICINE THEREOF

(71) Applicant: Zetang Wu, Anhui (CN)

(72) Inventor: Zetang Wu, Anhui (CN)

( * ) Notice: Subject to any disclaimer, the term of this patent is extended or adjusted under 35 U.S.C. 154(b) by 1062 days.

(21) Appl. No.: 17/614,970

(22) PCT Filed: May 28, 2020

(86) PCT No.: PCT/CN2020/093006
§ 371 (c)(1),
(2) Date: Nov. 29, 2021

(87) PCT Pub. No.: WO2020/239040
PCT Pub. Date: Dec. 3, 2020

(65) Prior Publication Data
US 2022/0168368 A1     Jun. 2, 2022

(30) Foreign Application Priority Data

May 30, 2019     (CN) ......................... 201910462073.5

(51) Int. Cl.
| | |
|---|---|
| *A61K 35/763* | (2015.01) |
| *A61P 35/00* | (2006.01) |
| *C12N 7/00* | (2006.01) |
| *C12N 15/85* | (2006.01) |

(52) U.S. Cl.
CPC ............ *A61K 35/763* (2013.01); *A61P 35/00* (2018.01); *C12N 7/00* (2013.01); *C12N 15/85* (2013.01)

(58) Field of Classification Search
CPC .. A61K 35/763; A61K 48/005; A61K 35/768; A61P 35/00; C12N 7/00; C12N 15/85; C12N 2310/14; C12N 2310/141; C12N 15/113; C12N 2710/16632; C12N 2710/16643; C12N 2710/16652; C12N 2710/16671; C12N 15/86; C12N 2800/107; C12N 2710/16621; Y02A 50/30
See application file for complete search history.

(56) References Cited

U.S. PATENT DOCUMENTS

| | | | | |
|---|---|---|---|---|
| 2005/0015824 A1* | 1/2005 | Scholer | .............. | G01N 33/5014 536/23.1 |
| 2005/0261218 A1* | 11/2005 | Esau | ....................... | A61P 37/00 536/23.1 |
| 2009/0143326 A1* | 6/2009 | Obad | ................... | A61K 31/713 536/24.5 |
| 2018/0339004 A1* | 11/2018 | Greenberg | ........... | C12N 15/113 |

FOREIGN PATENT DOCUMENTS

| | | | | |
|---|---|---|---|---|
| CN | 108884448 A | 11/2018 | | |
| CN | 109276580 A | 1/2019 | | |
| CN | 109568350 A | 4/2019 | | |
| CN | 110283794 A | 9/2019 | | |
| WO | WO-03012052 A2 * | 2/2003 | ........... | C12N 15/111 |

OTHER PUBLICATIONS

International Search Report (including English Translation) and Written Opinion with regard to PCT/CN2020/093006 mailed Sep. 3, 2020.
Office Action with regard to the CN Patent Application No. 201910462073.5 issued Aug. 12, 2020.
English Abstract for CN109568350 retrieved on Espacenet on Nov. 26, 2021.
English Abstract for CN110283794 retrieved on Espacenet on Nov. 17, 2021.
English Abstract for CN108884448 retrieved on Espacenet on Nov. 17, 2021.
English Abstract for CN109276580 retrieved on Espacenet on Nov. 17, 2021.
Ylosmaki E et al., "MicroRNA-mediated suppression of oncolyic adenovirus replication in human liver", PLOS One, vol. 8, No. 1, Jan. 2013, ISSN: 1932-6203.
Zhou, Feng et al., "(non-official translation: Oncolytic Viruses and Tumors)", (International Journal of Virology), vol. 16, No. 2., Apr. 2009, ISSN: 1673-4092.

* cited by examiner

*Primary Examiner* — Alexander W Nicol
(74) *Attorney, Agent, or Firm* — BCF LLP

(57) ABSTRACT

Provided are an oncolytic virus, a preparation method therefor, the use thereof and a medicine thereof, wherein the genome of the oncolytic virus includes the following exogenous elements: (1) a first expression cassette containing a first promoter and a first interfering RNA expression sequence; (2) a target sequence; and (3) a second expression cassette. The replication of the oncolytic virus is regulated and controlled by exogenous elements inserted into the genome sequence thereof; by means of the regulation and control by the exogenous elements, the oncolytic virus can be selectively replicated in different types of cells, and thus, second cells, that is, target cells (such as tumor cells), can be selectively killed, and first cells, that is, non-target cells (such as normal cells), are not damaged.

11 Claims, 4 Drawing Sheets

Specification includes a Sequence Listing.

RECOMBINANT ONCOLYTIC VIRUS, PREPARATION METHOD THEREFOR, USE THEREOF AND MEDICINE THEREOF

CROSS-REFERENCE TO RELATED APPLICATIONS

The present disclosure is a national stage entry under 35 U.S.C. § 371 of PCT/CN2020/093006, filed May 28, 2020, and claims the benefit of priority from Chinese Patent Application No. 201910462073.5, filed May 30, 2019, the entirety of each of which is incorporated herein by reference.

TECHNICAL FIELD

The present disclosure pertains to the field of biotechnology, and particularly to an oncolytic virus, a preparation method therefor, a use thereof, and a medicine thereof.

BACKGROUND

Cancers have become a main killer threatening human health. It has been shown according to data from *Global Cancer Statistics* 2015 that about 14.1 million new cancer cases were reported globally in 2015, and the death toll reached 8.2 million. 4.29 million new cancer cases were reported in China in 2015, and the number of death cases reached 2.81 million. Currently, cancer treatment mainly relies on by conventional surgical resection, radiotherapy and chemotherapy. Surgical resection can eradicate tumors or at least mitigate patients' suffering, but is not amenable to tumors located deep in the body due to lack of accessibility, and provides no help for already metastasized tumors. Radiotherapy and chemotherapy have long been used in clinic, but the application thereof is greatly limited due to the severe side effects derived from the non-selectivity between normal and tumor cells. In recent years, especially in the past five years, antibodies and CAR-T in treatment of cancers have attracted extensive attention. Antibody therapy can slow down the progression of cancers, but the therapeutic efficacy is far away from being satisfactory, and it has been widely believed antibody therapy is more suitable for use as an adjuvant therapy. Precise targeting can be achieved by CAR-T therapy, and CAR-T treatment might even cure cancers; however, CAR-T therapy might be mainly suited for treatment of hemological lymphomas, and one therapy is specifically for one patient, thus the cost for CAR-T treatment is extremely high. Moreover, the consequence of potential off-target engagement could be devastating or even deadly. In order to safely and efficiently treat cancers and relieve patients' suffering, it is highly desirable to develop a novel therapy for treatment using a completely new strategy. Among all the choices of options, genetically engineered oncolytic virus stands out because oncolytic viruses have been demonstrated to be safe while there is no concern for drug resistance, and hold the potential that one oncolytic virus could treat numerous tumors.

It was clinically observed as early as 100 years ago that viral infection slowed down tumor growth or even eradicated tumors. And then plasma or plasma extracts from hepatitis B patients were even used to treat Hodgkin's disease. However, people did not believe that a virus was a feasible option for cancer treatment, because there was no means to confer selectivity to a virus allowing for the virus to only replicate in tumors. In the 1990s, the progress in the molecular biological technology paved the way for genetically engineering a virus to specifically target tumor cells.

Early studies were focused on developing replication-defective lytic viruses such as adenovirus and replication defective non-lytic viruses such as adenovirus-associated virus to express immune-stimulatory molecules such as GMCSF, IL-12 and IL-17 or cytokines such as TNFα and IFNα for treatment of cancers by enhancing anti-tumor immunity. Since virus-based immunotherapies, like conventional immunotherapies, produce a limited therapeutic effect, therefore it has been thought that it should be used mainly as an adjuvant therapy. In order to fulfill the potential of viruses in cancer treatment, effort in recent years has been directed towards genetically modifying lytic viruses to confer the ability of the virus to specifically replicate in tumor cells (oncolytic virus). Such that the virus propagates in tumor cells, spread into the adjacent cells and kill them (oncolysis). Moreover, cellular debris derived from the lysed tumor cells can induce tumor-specific immunity, which help kill the tumor cells in the primary tumor site in return and destroy already metastasized tumor cells, thus producing the therapeutic benefits. Because of the demonstrated safety profile of oncolytic viruses and the potential of an oncolytic virus for treating a variety of cancers, the future of oncolytic viruses in treatment of cancers is highly anticipated. The approval by USA, EU, and Australia in 2015, 2016, respectively, for clinical use of a herpes virus type I-based oncolytic virus T-vec from the American company Amgen for treating melanoma, heralded a new era for treatment of cancers by oncolytic viruses. Research in oncolytic viruses has been growing tremendously since then, and as many as 80 clinical trials of oncolytic viruses for treating various tumors were conducted globally only in 2017. Many kinds of oncolytic viruses have been shown to perform well in pre-clinical studies, but in clinic, the therapeutic benefits are much less than expectation even though they have been shown to be clinically safe.

SUMMARY

The present disclosure provides a new oncolytic virus, the nucleotide sequences utilized for the generation and the method for preparing this virus, the potential use of the oncolytic virus for cancer treatment, and a composition containing the oncolytic virus and the like. The replication of the oncolytic virus is regulated and controlled by exogenous elements inserted into the viral genome thereof; through the regulation and control of viral gene expression by these exogenous elements, the oncolytic virus replicates differently in different cell types, and through the selective replication, target cells (such as tumor cells) can be selectively destroyed accordingly, while non-target cells (such as normal cells) are left intact.

Currently, selective replication of oncolytic viruses in cancer cells is achieved mainly by deleting one or more nonessential viral genes or by putting the expression of one or more essential viral genes under the control of a tumor-specific promoter. Viral nonessential genes are those genes which are not required for a virus to replicate in cultured cells. Viral replication does not require nonessential genes in vitro, but nonessential genes perform various functions to support viral replication in vivo, e.g. antagonizing the anti-viral mechanisms of a host or the like, so as to facilitate viral replication. For oncolytic viruses constructed by utilizing a tumor specific promoter to drive the expression of one or more essential genes, although the genome is kept intact, the temporally coordinated expression of viral genes is disrupted. Thus, the ability of the virus to replicate in vivo could be significantly impaired no matter whether a nonessential gene is deleted or an essential gene is expressed under the control of a tumor-specific promoter. Indeed, currently available oncolytic viruses generally perform poorly in clinical practice. In order to increase the effectiveness and expand the spectrum of the application of oncolytic viruses, it is crucial to keep the viral genome intact while not disrupting the highly coordinated expression of viral genes. With those as the guidelines a brand-new oncolytic virus was developed and prepared in the present disclosure using a novel strategy.

In a first aspect, the present disclosure provides an oncolytic virus with the genome of the oncolytic virus containing following exogenous elements:

(1) the first expression cassette containing the first promoter and the first interfering RNA expression sequence;

(2) the target sequence; and (3) the second expression cassette.

In the first expression cassette, the first interfering RNA expression sequence is used to express the first interfering RNA, which specifically binds to the target sequence; the first interfering RNA expression sequence is driven by the first promoter so as to express the first interfering RNA in first cells.

The target sequence is inserted into the 5' or the 3' untranslated region (UTR) of an essential viral gene in the viral genome.

The second expression cassette contains a second promoter and an inhibitory component expression sequence; the inhibitory component expression sequence is used to express inhibitory components. The inhibitory components are used to inhibit the biosynthesis and/or the bioactivity of one enzyme involved in the biosynthesis of the interfering RNA; and the inhibitory component expression sequence is driven by the second promoter so as to express the inhibitory components in second cells, but not in the first cells.

The first and second cells are different cell types.

As for the oncolytic virus provided in the present disclosure, the first expression cassette, the target sequence of the first interfering RNA, and the second expression cassette are inserted into the viral genome as shown in FIG. 1. The first interfering RNA is constitutively expressed in the first cells (non-target cells, such as normal cells) under the control of the first promoter after the cells are infected while the inhibitory components are specifically expressed with the expression driven by the second promoter in infected second cells (target cells, such as tumor cells). In the first cells, the first interfering RNA is constitutively expressed after the cells are infected, which binds to the interfering RNA target sequence located at the 5' or 3' UTR of an essential gene of the virus, thus resulting in cleavage of the targeted mRNA or preventing the essential gene from getting translated. As a result, no or much less amount of the regulated viral protein is produced leading to no viral replication with cells not affected. In contrast, in the second cells, the inhibitory components after the cells are infected by the virus, are specifically expressed from the viral genome under the control of the second promoter, which inhibit the biosynthesis, and/or bioactivity of the enzyme involved in the biosynthesis of interfering RNA, thus resulting in no or much less interfering RNA produced in those cells leading to robust viral replication and cell death. Strikingly differing from currently available oncolytic viruses, the oncolytic virus provided in the present disclosure possesses an intact genome while keeping the ability of the virus for the regulated viral genes to be expressed in a highly coordinated manner in the second cells, the two critical features required for an oncolytic virus to robustly replicate in tumor cells. Therefore, the oncolytic virus possesses the same or similar replication capacity as or to that observed with wild type virus in the second cells, thus killing tumor cells effectively. Based on the strategy, one can expect that when a tumor specific promoter, which is highly active in a variety of tumor cells, is used to drive the expression of the inhibitory components from the second expression cassette, the oncolytic virus would be used for treatment of various tumors.

Further, in certain embodiments of the present disclosure, the first expression cassette further contains a second interfering RNA expression sequence to express a second interfering RNA. The second interfering RNA acts on the open reading frame (ORF) of a nonessential viral gene of the oncolytic virus, so as to interfere with the expression of the nonessential gene, and the second interfering RNA expression sequence is expressed under the control of the first promoter.

The second interfering RNA after expressed in the first cells from the viral genome binds to the ORF of the nonessential gene of the virus, thus inhibiting the production of the nonessential gene product, which further enhances the safety of the virus in the first cells.

Further, in all the embodiments, the first interfering RNA and the second interfering RNA can be either a small interfering RNA (siRNA) or microRNA (miRNA).

Further, in certain embodiments of the present disclosure, the second cells are tumor cells of a mammal, and the first cells are non-tumor cells of a mammal.

Further, in certain embodiments of the present disclosure, the mammal refers to human.

Further, in certain embodiments of the present disclosure, the tumor cells are lung cancer cells, liver cancer cells, breast cancer cells, gastric cancer cells, prostate cancer cells, brain tumor cells, human colon cancer cells, cervical cancer cells, renal cancer cells, ovarian cancer cells, head and neck cancer cells, melanoma cells, pancreatic cancer cells, or esophageal cancer cells.

It should be noted that the oncolytic virus provided in the present disclosure is not limited to the selective killing of tumor cells, but may also be used to kill other non-tumor cells of interest. In other words, any cells of interest can serve as the second cells as mentioned above, that is, the target cells, while cells of no interest serve as the first cells, that is, the non-target cells. For example, any one kind of cells selected from nerve cells, red blood cells, white blood cells, blood platelets, phagocytes, epithelial cells, myocardial cells, ova, and sperms or the like can be killed as the second cells, that is to say, any cell originated from mammals can serve as the second cells, while one kind, several kinds, or all kinds of cells which are not selected as the second cells may serve as the first cells, and this oncolytic virus has no killing effect on these first cells.

In addition, it should also be pointed out oncolytic viruses generated using the concepts provided in the present disclosure, no matter what is the parental virus, all falls within the scope of protection of the present disclosure Further, in certain embodiments of the present disclosure, the target sequence is selected from the coding sequence of a gene of a non-mammal.

Preferably, in certain embodiments of the present disclosure, the target sequence of 19-23 nucleotides in length is selected from the ORF of a gene of the non-mammal.

Preferably, in certain embodiments of the present disclosure, the non-mammal is yeast, jellyfish, *Escherichia coli*, insect, fish, or plant.

Preferably, in certain embodiments of the present disclosure, the gene of the non-mammal can be selected from the group including green fluorescent protein gene derived from jellyfish, β-galactosidase gene derived from *Escherichia coli*, and luciferase gene derived from firefly.

Further, in certain embodiments of the present disclosure, the nucleotide sequence of the target is shown in SEQ ID NO1, and the sequence of the first interfering RNA is shown in SEQ ID NO: 2.

Further, in certain embodiments of the present disclosure, the target sequence is inserted into the 5' or the 3'UTR of one or more essential genes of the recombinant oncolytic virus.

Preferably, the copy number of the target sequence inserted at any position can be one or more.

Further, in certain embodiments of the present disclosure, the oncolytic virus is selected from a variety of viruses including herpes simplex virus (HSV), adenovirus, vaccinia virus, newcastle disease virus, poliovirus, coxsackie virus, measles virus, mumps virus, vesicular stomatitis virus (VSV), and influenza virus.

Preferably, when the oncolytic virus is herpes simplex virus, the essential gene is selected from the group including envelope glycoprotein L, uracil DNA glycosylase, capsid protein, helicase proenzyme subunit, DNA replication initiation binding unwindase, derived protein of myristic acid, deoxyribonuclease, coat serine/threonine protein kinase, DNA packaging terminase subunit 1, coat protein UL16, DNA packaging protein UL17, capsid triplex subunit 2, major capsid protein, envelope protein UL20, nucleoprotein UL24, DNA packaging protein UL25, capsid mature protease, capsid protein, envelope glycoprotein B, single-stranded DNA-binding protein, DNA polymerase catalytic subunit, nuclear egress layer protein, DNA packaging protein UL32, DNA packaging protein UL33, nuclear egress membrane protein, large capsid protein, capsid triplex subunit 1, ribonucleotide reductase subunit 1, ribonucleotide reductase subunit 2, capsule host shutoff protein, DNA polymerase processing subunit, membrane protein UL45, coat protein VP13/14, trans-activating protein VP16, coatprotein VP22, envelope glycoprotein N, coat protein UL51, unwindase-primaseprimase subunit, envelope glycoprotein K, ICP27, nucleoprotein UL55, nucleoprotein UL56, transcription regulation factor ICP4, regulatory protein ICP22, envelope glycoprotein D and membrane protein US8A; and the nonessential gene is selected from ICP34.5, ICPO, nucleoprotein UL3, nucleoprotein UL4, helicase proenzyme helicase subunit, cuticular protein UL7, envelope glycoprotein M, coat protein UL14, coat protein UL21, envelope glycoprotein H, thymidine kinase, DNA packaging terminating enzyme subunit 2, small capsid protein, coat protein UL37, envelope protein UL43, envelope glycoprotein C, coat protein VP11/12, uracil deoxyribosidetriphosphatase, viral protein US2, serine/threonine protein kinase U3, membrane G glycoprotein (envelope glycoprotein G), envelope glycoprotein J, envelope glycoprotein I, envelope glycoprotein E, membrane protein US9, viral protein US10, cuticular protein Us11, and ICP47.

Preferably, when the oncolytic virus is adenovirus, the essential gene is selected from the group including early protein 1A, early protein 1B 19K, early protein 1B 55K, encapsidation protein Iva2, DNA polymerase, terminal protein precursor pTP, encapsidation protein 52K, capsid protein precursor pIIIa, pentomer matrix, core protein pVII, core protein precursor pX, core protein precursor pVI, hexonmer, proteinase, single-stranded DNA-binding protein, hexamer assembly protein 100K, protein 33K, encapsidation protein 22K, capsid protein precursor, protein U, fibrin, open reading frame 6/7 of regulatory protein E4, regulatory protein E4 34K, open reading frame 4 of regulatory protein E4, open reading frame 3 of regulatory protein E4, open reading frame 2 of regulatory protein E4, and open reading frame 1 of regulatory protein E4; and the nonessential gene is selected from the group including capsid protein IX, protein 13.6K, core protein V, regulatory protein E3 12.5K, membrane glycoprotein E3 CR1-α, membrane glycoprotein E3 gp19K, membrane glycoprotein E3 CR1-β, membrane glycoprotein E3 CR1-δ, membrane glycoprotein E3 RID-δ, and membrane glycoprotein E3 14.7K.

Preferably, when the oncolytic virus is vaccinia virus, the essential gene is selected from the group including ribonucleotide reductase small-subunit, serine/threonine kinase, DNA-binding viral core protein, polymerase large-subunit, RNA polymerase subunit, DNA polymerase, sulfhydryl oxidase, hypothetical DNA-binding viral nucleoprotein, DNA-binding phosphoprotein, nucleoid cysteine proteinase, RNA helicase NPH-II, hypothetical metalloproteinase, transcription elongation factor, glutathione-type protein, RNA polymerase, hypothetical viral nucleoprotein, late transcription factor VLTF-1, DNA-binding viral nucleoprotein, viral capsid protein, polymerase small-subunit, RNA polymerase subunit rpo22 depending on DNA, RNA polymerase subunit rpo147 depending on DNA, serine/threonine protein phosphatase, IMV heparin-binding surface protein, DNA-dependent RNA polymerase, late transcription factor VLTF-4, DNA topoisomerase type I, mRNA capping enzyme large-subunit, viral core protein 107, viral core protein 108, uracil-DNA glycosylase, triphosphatase, 70 kDa small subunit of early gene transcription factor VETF, RNA polymerase subunit rpo18 depending on DNA, nucleoside triphosphate hydrolase-I, mRNA capping enzyme small-subunit, rifampicin target site, late transcription factor VLTF-2, late transcription factor VLTF-3, disulfide bond forming pathway, precursor p4b of core protein 4b, core protein 39 kDa, RNA polymerase subunit rpo19 depending on DNA, 82 kDa large subunit of early gene transcription factor VETF, 32 kDa small subunit of transcription factor VITF-3, IMV membrane protein 128, precursor P4a of core protein 4a, IMV membrane protein 131, phosphorylated IMV membrane protein, IMV membrane protein A17L, DNA unwindase, viral DNA polymerase processing factor, IMV membrane protein A21L, palmitoyl protein, 45 kDa large subunit of intermediate gene transcription factor VITF-3, RNA polymerase subunit rpo132 depending on DNA, RNA polymerase rpo35 depending on DNA, IMV protein A30L, hypothetical ATP enzyme, serine/threonine kinase, EEV mature protein, palmitoylated EEV membrane glycoprotein, IMV surface protein A27L, EEV membrane phosphate glycoprotein, IEV and EEV membrane glycoproteins, EEV membrane glycoprotein, disulfide bond forming pathway protein, hypothetical viral nucleoprotein, IMV membrane protein 12L, poxvirus myristoyl protein, IMV membrane protein L1R, late 16 kDa hypothetical membrane protein, hypothetical virus membrane protein H2R, IMV membrane protein A21L, chemokine-binding protein, epidermal growth factor-like protein, and IL-18 binding protein; and the nonessential gene is selected from the group including secretory complement binding protein, kelch-like protein, virulence factors, hypothetical α-amino protein sensitive protein, serpin-type protein, phospholipase D-type protein, unfeatured protein K7R, CD47-type hypothetical membrane protein, alarmone-type protein, C-type agglutinin-type type II membrane protein, secretory glycoprotein, uracil deoxyribosidetriphosphatase, kelch-like protein F3L, hypothetical myristoylated protein, ribonucleotide reductase large-subunit, vaccinia virus type A inclusion body protein, ankyrin-type protein, 6 kda intracellular viral protein, tumor necrosis factor α-receptor-like protein 215, tumor necrosis factor α-receptor-like protein 217, ankyrin-type protein B4R, ankyrin-type protein 213, ankyrin-type protein 211, zinc finger protein 207, zinc finger protein 208, ankyrin-type protein 014, ankyrin-type protein 015, ankyrin-type protein 016, ankyrin-type protein 017, ankyrin-type protein 019, ankyrin-type protein 030, hypothetical monoglyceride lipase 036, hypothetical monoglyceride lipase 037, hypothetical monoglyceride lipase 038, ankyrin-type protein 199, ankyrin-type protein 203/hypothetical protein, type A inclusion body protein, guanylate kinase, and ankyrin-type protein 188.

Preferably, when the oncolytic virus is coxsackie virus, the essential gene is selected from the group including protein Vpg, core protein 2A, protein 2B, RNA unwindase 2C, protein 3A, proteinase 3C, reverse transcriptase 3D, coat protein Vp4, and protein Vp1; and the nonessential gene is either capsid proteins Vp2 or Vp3.

Preferably, when the oncolytic virus is measles virus, the essential gene is selected from the group including nucleo-protein N, phosphoprotein P, matrix protein M, transmem-brane glycoprotein F, transmembrane glycoprotein H, and RNA-dependent RNA polymerase L; and the nonessential gene is either RNA-dependent RNA polymerase accessory protein C or RNA-dependent RNA polymerase accessory protein V.

When the oncolytic virus is mumps virus, the essential gene is selected from the group including nucleoprotein N, phosphoprotein P, fusion protein F, and RNA polymerase L; and the nonessential gene is selected from the group including phosphoprotein V, membrane protein M, and hemagglu-tinin neuraminidase protein HN.

Preferably, when the oncolytic virus is vesicular stoma-titis virus, the essential gene is selected from the group including glycoprotein G, nucleoprotein N, phosphoprotein P, and RNA polymerase L; and the nonessential gene is matrix protein M.

Preferably, when the oncolytic virus is poliovirus, the essential gene is selected from the group including capsid protein VP1, capsid protein VP2, capsid protein VP3, cys-teine protease 2A, protein 2B, protein 2C, protein 3A, protein 3B, proteinase 3C, protein 3D, and RNA-directed RNA polymerase; and the nonessential gene is capsid pro-tein VP4.

Preferably, when the oncolytic virus is influenza virus, the essential gene is selected from the group including hemag-glutinin, neuraminidase, nucleoprotein, membrane protein M1, membrane protein M2, polymerase PA, polymerase PB1-F2, and polymerase PB2; and the nonessential gene is either non-structural protein NS1 or non-structural protein NS2.

Further, in certain embodiments of the present disclosure, the oncolytic virus is herpes simplex virus type-1, the essential gene is ICP27, and the nonessential gene is ICP34.5.

Further, in certain embodiments of the present disclosure, the sequence of the second interfering RNA is shown in SEQ ID NO:3.

Further, in certain embodiments of the present disclosure, the first promoter is a constitutive promoter.

Preferably, when the target sequence is inserted into the 5' or the 3' UTR of multiple essential genes, the first expression cassette only expresses the first interfering RNA, and the first promoter is either human Hu6 or H1 promoter.

Preferably, when the target sequence is inserted into the 5' or 3' UTR of only one essential gene and the ORF of a non-essential gene is targeted by the second interfering RNA, the first expression cassette expresses the first and the second interfering RNA simultaneously, and the first pro-moter is selected from the group including CMV, SV40, and CBA promoters.

Further, in certain embodiments of the present disclosure, the second promoter is a human tumor-specific promoter.

Preferably, the human tumor-specific promoter is selected from telomerase reverse transcriptase promoter (hTERT), human epidermal growth factor receptor-2 (HER-2) pro-moter, E2F1 promoter, osteocalcin promoter, carcinoembry-onic antigen promoter, survivin promoter, and ceruloplasmin promoter.

Further, in certain embodiments of the present disclosure, the enzyme is any of Drosha, Dicer, and Agonauts.

Further, in certain embodiments of the present disclosure, the inhibitory components contain the third interfering RNA to interfere with the gene expression of an enzyme to inhibit the biosynthesis of interfering RNA.

Preferably, the enzyme is Drosha.

Further, in certain embodiments of the present disclosure, the base sequence of the third interfering RNA is shown in SEQ ID NO:4.

Further, in certain embodiments of the present disclosure, the inhibitory component further contains an expanded nucleotide triplet repeats' RNA for inhibiting the Drosha activity or a non-coding RNA for inhibiting Dicer activity.

Preferably, the expanded nucleotide triplet repeats' sequence has the following general formula: $(CGG)n$, wherein n is an integer number equal to or greater than 20.

Preferably, n ranges from 60 to 150.

Preferably, n equals to 100.

Preferably, the non-coding RNA for inhibiting the Dicer activity is adenovirus type 5 VA1 RNA.

Preferably, the nucleotide sequence of the adenovirus type 5 VA1 RNA is shown as follows (SEQ ID NO: 8):

```
AGCGGGCACUCUUCCGUGGUCUGGUGGAUAAAUUCGCAAGGGUAUCA

UGGCGGACGACCGGGGUUCGAGCCCCGUAUCCGGCCGUCCGCCGUGA

UCCAUGCGGUUACCGCCCGCGUGUCGAACCCAGGUGUGCGACGUCAG

ACAACGGGGGAGUGCUCCUUU.
```

Further, in certain embodiments of the present disclosure, the second expression cassette further contains an enhancer sequence to enhance the expression of the inhibitory com-ponents.

Preferably, the enhancer is either CMV or SV40 enhancer.

Further, in certain embodiments of the present disclosure, the preservation number of the foregoing oncolytic virus is CCTCC NO. V201919. This virus has been preserved at China Center for Type Culture Collection (CCTCC) situated in Wuhan University, Luojiashan, Wuchang, Wuhan City on Apr. 24, 2019.

In a second aspect, the present disclosure further provides another oncolytic virus (the second kind of oncolytic viruses), the genome of the oncolytic virus containing fol-lowing exogenous elements: a target sequence of an inter-fering RNA and an interfering RNA expression cassette, wherein the expression cassette contains a promoter and an interfering RNA expression sequence, and the interfering RNA expression sequence is used for expressing the inter-fering RNA, which binds to the target sequence.

In the second kind of oncolytic viruses, the RNA target sequence is inserted into the 5' or the 3' UTR of one or more than one essential gene in the genome of the recombinant oncolytic virus.

Expression of the interfering RNA is driven by a promoter specific to first cells, so as to express RNA in the first cells but not in second cells.

The first and second cells are different cell types.

The second kind of oncolytic viruses does not contain the second expression cassette. The expression of the interfering RNA from the expression cassette thereof is driven by a promoter specific to first cells, which drives the expression of the interfering RNA only in the first cells, but not in the second cells. In the first cells, the interfering RNA is expressed from the viral genome after the cells are infected by the virus and binds to the interfering RNA target sequence thus preventing or inhibiting the translation of the essential gene(s); As a result, the virus does not replicate and the cells are safe. In the second cells, the interfering RNA is not expressed because of lack of the promoter activity in the cells, resulting in a robust expression of the regulated essential gene, which leads to viral replication and kill the cells.

The oncolytic virus of the two kinds mentioned above can both achieve selective replication in the second cells while leaving the first cells unaffected such that normal cells are safe.

Further, in certain embodiments of the present disclosure, the first cells are non-tumor cells of a mammal, and the second cells are tumor cells.

In a third aspect, the present disclosure provides nucleotide sequences for generating the oncolytic virus as described above, the nucleotide sequences contain one or more following elements:

the target sequence, the first expression cassette, and the second expression cassette.

In a fourth aspect, the present disclosure provides methods of constructing plasmids for preparing complementing host cells, the parental virus and a oncolytic virus as described above.

Compared to the genome sequence of wild-type virus, an essential gene is absent in the genome of the parental virus.

The complementing host cells contain a DNA fragment for expressing the essential gene, which is absent from the parental virus.

In a fifth aspect, the present disclosure provides a method of preparing the oncolytic virus as described above, comprising integration of a nucleotide sequence as described above into the viral genome.

Further, in certain embodiments of the present disclosure, this preparation method comprises: cell culture, virus infection of the complementing cells with the parental virus followed by transfection of the cells with plasmid DNA, screening and identification of the recombinant oncolytic virus.

In a sixth aspect, the present disclosure provides use of the oncolytic virus as described above for selectively killing cells.

Further, in certain embodiments of the present disclosure, the cells are tumor cells.

In a seventh aspect, the present disclosure provides a method of killing cells, comprising: infection of oncolytic virus target cells with the oncolytic virus as described above.

Further, in certain embodiments of the present disclosure, the target cells are tumor cells.

Further, in certain embodiments of the present disclosure, the method aims at non-disease treatment.

In an eighth aspect, the present disclosure provides a medicine for killing cells, which contains the oncolytic virus as described above and a clinically acceptable adjuvant.

Further, in certain embodiments of the present disclosure, the cells are tumor cells.

In a ninth aspect, the present disclosure provides a method of detecting the oncolytic virus as described above with detailed steps including: titer determination of the oncolytic virus, propagation of the oncolytic virus, purification of the oncolytic virus, mRNA expression analysis, protein expression analysis, and miRNA expression analysis.

The present disclosure further provides a method of treating the disease in clinic, comprising administration of the oncolytic virus or combinatorial therapies containing the virus provided in the present disclosure, wherein the disease is derived from the second cells.

In one or more embodiments, the disease is cancer, and the second cells are tumor cells.

The present disclosure further provides use of the oncolytic virus according to the present disclosure for selectively killing cells.

In one or more embodiments, the cells are tumor cells.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION OF THE EMBODIMENTS

Figure 1:
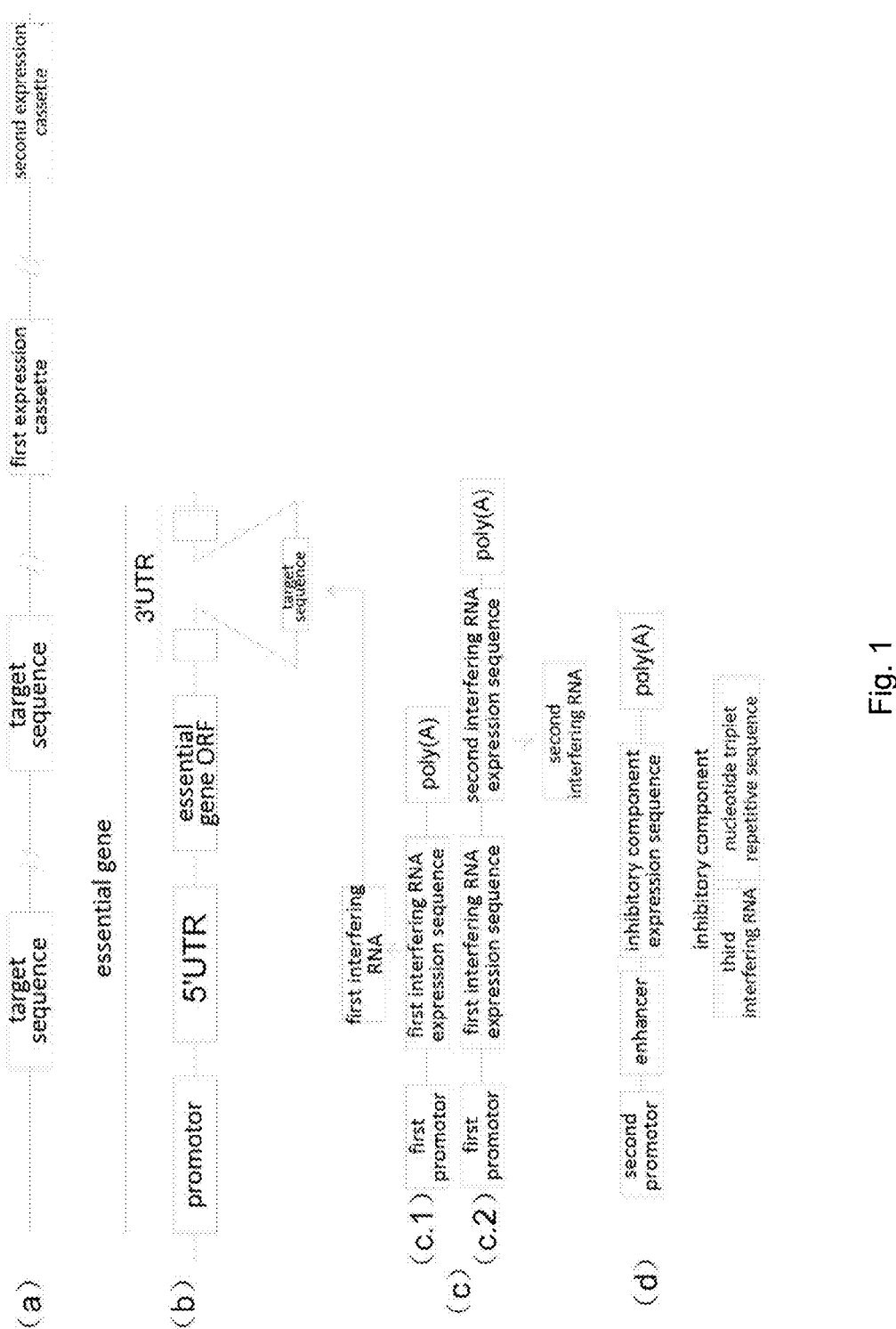
FIG. 1: Schematic representation of exogenous elements inserted into the genome of an oncolytic virus provided in the present disclosure: (a): Elements inserted into the genome, wherein the copy number of the target sequence can be one or more; (b): Location of the target sequence inserted into an essential viral gene; (c): Expression of the first interfering RNA in the first cells (c1), and simultaneous expression of the first and the second interfering RNAs in the first cells (c2). The first promoter is a constitutive one, which drives continuous expression of interfering RNAs in the first cells. The first interfering RNA targets an essential gene(s) by binding to the target sequence inserted into the 3' UTR of one essential gene or genes. The second interfering RNA targets the ORF of a non-essential gene. (d): Specific expression of the inhibitory components in the second cells, which inhibits the biosynthesis of interfering RNAs. The inhibitory components include an interfering RNA and an expanded nucleotide triplet repeats' RNA.

In order to demonstrate the features of the present disclosure, its nature and various advantages, exemplary embodiments were executed and are described in details below. All experiments were conducted using standard methods as described in literature. Reagents were purchased from commercial providers and used according to the instruction of the manufacturer.

As used herein, terms "base sequence" and "nucleotide sequence" can be used interchangeably, and generally refer to the composition and order of nucleotides arranged in DNA or RNA.

The term "primer" refers to a synthetic oligonucleotide, which is required for de novo nucleic acid synthesis. After binding to a polynucleotide template, the primer is extended in 5' to 3' direction along the template catalyzed by DNA polymerase, hereby producing an extended duplex. Nucleotide addition during the extension is determined by the sequence of the template. A primer is typically 18-23 nucleotides in length. However, a primer length is determined by several factors including the nucleotide composition and the melting point of the primer, and the downstream application of the PCR product after amplified.

The term "promoter" generally refers to a DNA sequence that is located upstream of the 5'-UTR of a gene, can be specifically identified and bound to by an RNA polymerase, and is required by transcription.

The term "enhancer" refers to a DNA sequence that increases transcription frequency of the gene interlocked therewith. The enhancer enhances the transcription by increasing the activity of a promoter. An enhancer may be located either at the 5'end or the 3'end of a gene, and even may exist as an intron within a gene. An enhancer might significantly affect gene expression, which might increase the gene transcription by 10-200 folds, or even by thousand times.

As used herein, the term "interfering RNA" refers to a RNA molecule that can binds to its target sequence thus inhibiting the expression of the target gene. Interfering RNA molecules comprise, but are not limited to, a short hairpin RNA (shRNA), siRNA, microRNA (miRNA), synthesized 21-23 nt RNA duplex.

Terms "subject", "individual", and "patient" can be used interchangeably herein, and refer to a vertebrate, preferably a mammal, most preferably human. The mammal comprises, but is not limited to, mouse, ape, human, domesticated animal, or farm-raised livestock.

The features and its nature of the present disclosure are described in detail below with reference to examples.

Example 1

Generation of a Recombinant Oncolytic Virus

The oncolytic virus provided in the present example was developed by inserting exogenous elements into the genome of herpes virus type-1 (HSV-1) wild-type virus KOS by homologous recombination. The genome of this oncolytic virus has following structural features.

(1) Consisting of three elements inserted: EGFP miRNA target sequence inserted into the 3' UTR of HSV-1 essential gene ICP27 followed by SV 40 poly(A), the first expression cassette, and a second expression cassette. The target sequence of EGFP miRNA is a small portion of the EGFP coding sequence, which is hereinafter referred to as EGFP miRNA target sequence. The first and second expression cassettes are located between SV40 Poly (A) and ICP27 3' UTR. The first expression cassette expresses both EGFP mina and ICP34.5 mina. ICP34.5 mina binds to ICP34.5 ORF. The second expression cassette expresses saran to target Dorsa ORF and CGG repeats to inhibit Dorsa activity.

(2) The first expression cassette included: CMV promoter, EGFP miRNA expression sequence (the first miRNA), and ICP34.5 miRNA expression sequence (the second interfering RNA followed by SV40 Poly(A) sequence I.

(3) The second expression cassette including: a hybrid promoter consisting of tumor specific hTERT promoter fused with a CMV enhancer, the inhibitory component expression sequence to simultaneously expresses Drosha siRNA and CGG triplet repeats and a Poly(A) sequence located downstream the inhibitory component expression sequence.

This oncolytic virus oHSV-BJR was prepared according to the following methods. Firstly, the complementing cells expressing ICP27 were established with African green monkey kidney cells (Vero cells) as the starting material, so to support the preparation, identification and propagation of the recombinant viruses. Secondly, the parental virus HSV-EGP, in which HSV-1 ICP27 is replaced by EGFP, was generated by homologous recombination between a plasmid and wild-type KOS with the complementing cells as the host. Thirdly, oHSV-BJR was generated by homologous recombination between a plasmid and the parental virus HSV—with the complementing cells as the host. Detailed experimental steps were as follows.

(1) Preparation of the Complementing Cells Expressing ICP27

Figure 2:
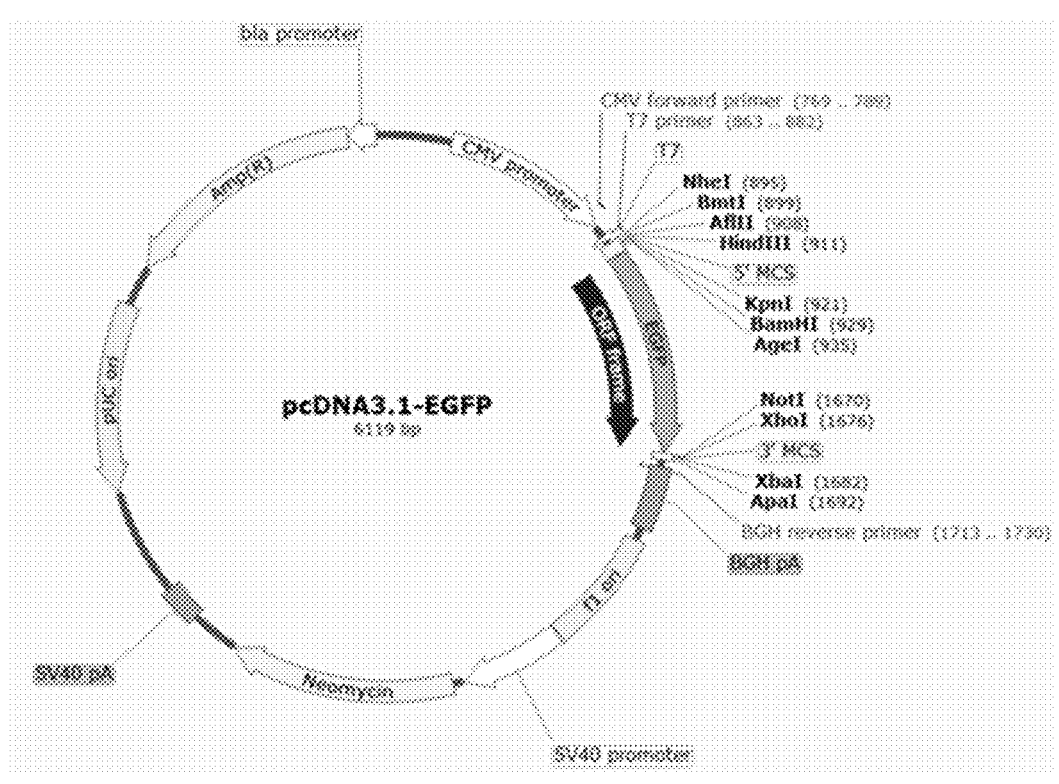
FIG. 2: Schematic showing of the parental plasmid pcDNA3.1-EGFP unitized for constructing a plasmid expressing HSV-1 ICP27. In the plasmid, EGFP is constitutively expressed under the control of CMV promoter and the plasmid contains the neomycin-resistant gene expression sequence.

The wild-type herpes virus KOS DNA was used as template, the coding region of the ICP27 gene was amplified by PCR, and the amplified fragment was inserted into the sites of HindIII and XbaI of plasmid pcDNA3.1-EGFP (seen in FIG. 2) to replace the ORF of EGFP. The resulting plasmid was named as pcDNA3.1-10P27. In plasmid pcDNA3.1-10P27, HSV-1 ICP27 gene was expressed under the control of CMV promoter. Also, neomycin-resistant gene is expressed from plasmid pcDNA3.1-10P27 in mammalian cells for facilitating complementing cell screening.

Vero cells were treated with G418 of different concentrations, the culture medium containing G418 was replaced every three days with media containing G418 of different concentrations, and cell death was monitored every day. The minimal concentration of G418 required for all cells to dies after 6 days of G418 treatment was determined. Such a concentration of G418 (500 µg/ml) was utilized for complementing cell establishment.

$3.5 \times 10^5$ Vero cells were seeded into wells of a 6-well cell culture plate and cultured overnight in an antibiotic-free media. Cells were transfected with ICP-27-expressing plasmid using Lipofectamine 2000 as transfection reagent (4 µg DNA/well), and harvested 24 hrs after transfection. Cells were diluted using 500 µg/ml G418-containing medium, by 5, 10, 20, 40, 60-fold. 3 ml cells of each dilution were seeded in wells of 6-well plates. Medium was changed every three days for a total of 6 to 7 times. When cell clones reached 3-4 mm in diameter, cell clones picked using a clone cylinder. Cells from each clone were propagated gradually from a well of a 24-well plate to T150 culture flasks. Proteins were isolated, and expression of ICP27 from cells derived from each clone was analyzed using Western blot. Cells with the highest level of ICP27 expression were selected as the complementing cells to support the growth and replication of replication-defective viruses in which ICP27 are not expressed; the cells were named as $C_{ICP27}$. The complementing cell has been preserved at China Center for Type Culture Collection (CCTCC) situated in Wuhan University, Luojiashan, Wuchang, Wuhan City on Apr. 24, 2019 with a preservation number of CCTCC NO. C201974.

(2) Generation of the Parental Virus

The parental virus HSV-EGFP, in which HSV-1 ICP27 is replaced by EGFP gene in the genome, was developed by homologous recombination between a plasmid and the wild-type herpes virus KOS. The construction of the parental virus was to facilitate the screening of the oncolytic virus in the subsequent steps.

DNA fragment A including the 5'UTR of the ICP27 gene, CMV promoter, the EGFP ORF, a bovine growth hormone Poly(A) (BGH Poly(A)), and a 3'UTR of the ICP27 gene was synthesized with the nucleotide sequence shown in SEQ ID NO:5. The detailed description of fragment A is given below site 1-6: an irrelevant sequence for increasing the terminal length to facilitate enzymatic cleavage;

site 7-12: XhoI site, C/TCGAG;

site 13-575: ICP27 5' UTR;

site 576-1163: CMV promoter;

site 1164-1174: spacer;

site 1175-1180: Kozak sequence for strengthening protein translation;

site 1181-1900: EGFP ORF, site 1901-2144: BGH Poly (A);

site 2145-2667: ICP27 3' UTR;

site 2668-2773: HindIII site, A/AGCTT, and site 2774-2779: an irrelevant sequence for increasing the terminal length to facilitate enzymatic cleavage.

The DNA fragment A was cleaved and ligated to the sites of HindIII and XhoI of plasmid pcDNA3.1-EGFP. The resulting plasmid was named as EGFP expression plasmid.

$3.5 \times 10^5$ complementing $C_{ICP27}$ cells were seeded into each well of a 6-wellplate and cultured overnight in an antibiotic-free media. Cells of each well were infected with 0.1, 0.5, 1 or 3 MOI (virus/cell) wild-type virus KOS and transfected with the EGFP expression plasmid obtained from the previous step (4 µg DNA/well) using Lipofectamine 2000 as the transfection reagent 1 hr after infection.

Complete medium was substituted for the transfection mixture in the 6-well plate 4 hrs after transfection. After all the cells showed cytopathic expression and became rounded, cells in media were harvested. The cell mixtures after three cycles of freeze and thaw were centrifuged and supernatants collected.

The supernatants were diluted, and the complementing $C_{ICP27}$ cells were infected by the virus of different dilutions, and viruses separated by plaque assay with overlaid semi-solid methyl cellulose as support media. After 4-5 days of infection, plaques were screened under a fluorescence microscope and green plaques picked. And 2-3 more rounds of screening were conducted until pure green plaques were obtained under a fluorescence microscope. The plaque with the brightest green fluorescence was picked and propagated using the complementing $C_{ICP27}$ cells as the host. The obtained virus was the parental virus HSV-EGFP.

(3) Construction of ICP27 and Regulatory Components-Containing Plasmid

TA cloning plasmid was modified, such that the multiple cloning site in the plasmid contains an Xho1 site. The resulting plasmid was named as plasmid TA-Xho1.

DNA fragment B containing an ICP27 5' UTR with the endogenous ICP27 promoter included, the ICP27 ORF, two copies of the target sequence inserted in tandem (a single-copied EGFP miRNA target sequence is shown in SEQ ID NO:1 and in Table 1), and SV40 Poly(A) sequence followed by ICP27 3' UTR sequence (the 5' and the 3' of the DNA fragment both contain one XhoI site; and one HindIII site was inserted between SV40 Poly(A) and the ICP27 3' UTR sequence), was synthesized; and the nucleotide sequence of the DNA fragment B is shown in SEQ ID NO:6, wherein. The detailed information of DNA fragment B is given below.

site 1-6: an irrelevant extra sequence for increasing the terminal length facilitate enzymatic cleavage;

site 7-12: Xho1 site, C/TCGAG, site 13-683: ICP27 5'UTR including ICP27 promoter;

site 684-2222: ICP27 ORF;

site 2223-2227: spacer sequence;

site 2228-2249 and 2253-2274: EGFP miRNA target sequence (SEQ ID NO:1);

site 2250-2252: spacer;

site 2275-2800: SV40 Poly(A);

site 2801-2806: HindIII site, A/AGCTT, site 2807-3326: ICP27 3'UTR;

site 3327-3332: Xho1 Site; and site 3333-3338: an irrelevant sequence for increasing the terminal length so to facilitate enzymatic cleavage.

The DNA fragment B was cleaved by XhoI, and inserted into the XhoI site of the plasmid TA-XhoI. The resulting plasmid was named as plasmid TA-XhoI-mICP27.

DNA fragment C including a CMV promoter, the EGFP miRNA expression sequence, the ICP34.5 miRNA expression sequence, BGH Poly(A), the hTERT-CMV hybrid promoter, a Drosha siRNA expression sequence, and a CGG-triplet-repeat expression sequence followed by SV40 Poly(A), was synthesized. DNA fragment C contains one HindIII site at the 5' and 3' ends, respectively. The base sequence of DNA fragment C is shown in SEQ ID NO:7, with details given as follows:

site 1-8: an irrelevant sequence for increasing the terminal length to facilitate the enzymatic cleavage;

site 9-14: HindIII site, A/AGCTT, site 15-629: CMV promoter;

site 630-706: EGFP miRNA expression sequence (the sequence shown in SEQ ID NO:2 and in table 2);

site 707-762: an irrelevant sequence serving as spacer;

site 763-830: ICP34.5 miRNA expression sequence (the sequence shown in SEQ ID NO:3 and in table 1);

site 831-989: an irrelevant sequence serving as spacer;

site 990-1213: BGH Poly(A)

wherein the sequence from nucleotide 15 to 1213 represents the first expression cassette;

site 1214-1660 (reverse-complementary): SV40 Poly(A);

site 1661-1667 (reverse-complementary): an irrelevant sequence serving as spacer;

site 1668-1967 (reverse-complementary): CGG triplet repeats (the general formula of the triplet repeats is (CGG)100;

site 1968-1976 (reverse-complementary): an irrelevant sequence serving as spacer;

site 1977-2026 (reverse-complementary): Drosha siRNA expression sequence (sequence shown in SEQ ID NO:4, and in Table 1 f);

site 2027-2044 (reverse-complementary): an irrelevant sequence serving as spacer;

site 2045-2152 (reverse-complementary): CMV enhancer;

site 2153-2608 (reverse-complementary): hTERT promoter;

sequence from nucleotide 214 to 2608 represents a second expression cassette (reverse-complementary);

site 2609-2614: HindIII site, A/AGCTT, site 2615-2622: irrelevant sequence for increasing the terminal length to facilitate enzymatic cleavage.

DNA fragment C was cleaved by HindIII and inserted into the HindIII site of plasmid TA-XhoI-mICP27 obtained from the previous step to produce a plasmid TA-XhoI-mICP27-REG-RNA for preparing a recombinant oncolytic virus.

TABLE 1

| name | sequence (5'-3') | SEQ ID NO: |
|---|---|---|
| EGFP miRNA target sequence | CAAGCTGACCCTGAAG TTCATA | 1 |
| EGFP miRNA (first interfering RNA in the present example) | AUGAACUUCAGGGUCA GCUUG | 2 |
| ICP34.5 miRNA (second interfering RNA in the present example) | CUUGCCUGUCUAACUC GCUAGU | 3 |
| Drosha siRNA (third interfering RNA in the present example) | CUUGCUGAAUACUUGG UCCUUGGUG | 4 |

(4) Construction of Oncolytic Herpes Virus oHSV-BJR

An oncolytic herpes virus was constructed by homologous recombination between plasmid TA-XhoI-mICP27-REG-RNA and the parental virus HSV-EGFP in complementing $C_{ICP27}$ cells.

The manipulations were as follows.

$3.5\times10^5$ complementing $C_{ICP27}$ cells were seeded into a 6-well cell plate and cultured overnight in an antibiotic-free media. The cells of each well were infected with 0.1, 0.5, 1 or 3 MOI the parental virus HSV-EGFP, respectively and transfected with the recombinant plasmid TA-XhoI-mICP27-REG-RNA (4 µg DNA/well) using Lipofectamine 2000 as the transfection reagent 1 hr later. Complete medium was substituted for the transfection mixture 4 hrs after transfection. After all the cells showed cytopathic expression, and became rounded, cells in media harvested. The cell mixtures after three cycles of freeze and thaw were centrifuged and supernatants collected. The supernatants were diluted, and complementing $C_{ICP27}$ cells were infected by diluted viruses. Viruses were separated by plaque assay with overlaid semi-solid methyl cellulose as support media. After 4-5 days of incubation, plaques were screened under a fluorescence microscope and black plaques picked. 2-3 more rounds of screening were conducted until pure plaques were obtained under a fluorescence microscope. Viruses from several pure plaques were propagated using complementing $C_{ICP27}$ cells as the host. Infected cell DNA was isolated. The recombinant virus was identified by PCR amplification using specific primers and sequencing. The recombinant virus was named as oHSV-BJ R.

Oncolytic virus oHSV-BJR has been preserved at China Center for Type Culture Collection (CCTCC) situated in Wuhan University in Luojiashan, Wuchang, Wuhan City on Apr. 24, 2019 under the preservation number CCTCC NO. V201919.

Figure 3:
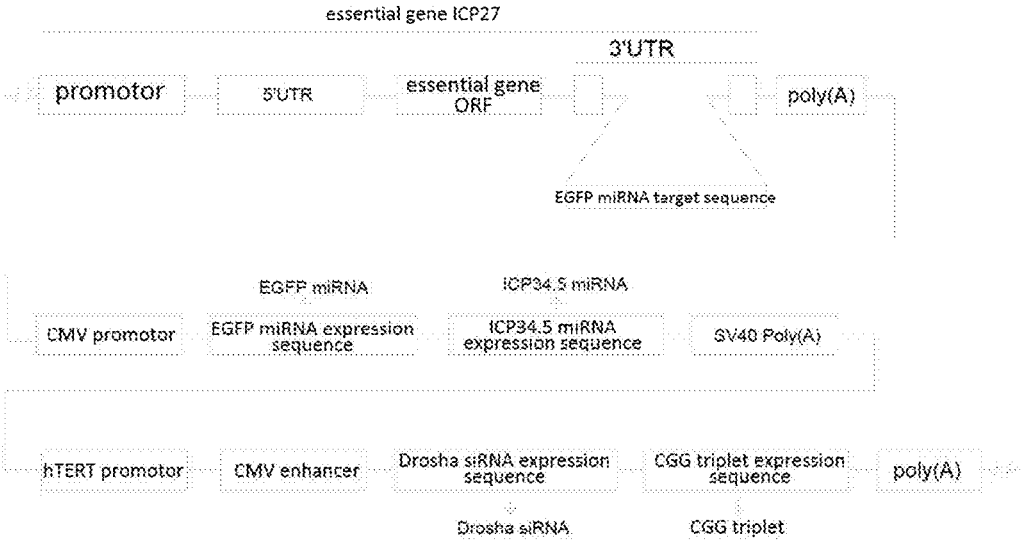
FIG. 3: Schematic of exogenous elements inserted into the genome of the oncolytic virus oHSV-BJR in an embodiment of the present disclosure.

The exogenous elements inserted and their locations in the genome are shown in FIG. 3:

the EGFP miRNA target sequence and SV40 Poly(A) sequence were inserted into the 3'UTR of the essential gene ICP27, the first expression cassette was located downstream SV40 Poly(A) sequence, including CMV promoter, the EGFP miRNA expression sequence, the ICP34.5 miRNA expression sequence, and BGH Poly(A); and the second expression cassette, was located downstream the first expression cassette, including a hTERT-CMV hybrid promoter, the Drosha siRNA expression sequence, the CGG-triplet-repeat expression sequence, and SV40 Poly(A) sequence (the second expression cassette is reverse-complementary relative to the first expression cassette).

Example 2

Titer analysis, propagation and purification of the oncolytic virus; miRNA, mRNA, and protein expression analysis; and tumor cell killing test (1) Titer Determination of the Oncolytic Virus oHSV-BJR $3.5 \times 10^5$ complementing $C_{ICP27}$ cells were seeded into a 6-well plate and cultured overnight in complete media. A serial of 10-fold dilutions of the virus stock obtained from example 1 was performed, and the cells in wells infected with 0.1 ml of virus of each dilution, respectively. The media in wells was aspirated 1 hr later and 3 ml of complete medium containing 1.25% methyl cellulose added to each well. The cells were incubated at 37° C. in a 5% $CO_2$ incubator for 4-5 days. 0.1% crystal violet prepared in 50% methanol and 50% ethanol was added to the wells and washed to remove the dye by tap water, and plaques counted. Virus titer (PFU/ml) was calculated.

(2) Propagation of Oncolytic Virus oHSV-BJR $5.5 \times 10^6$ complementing $C_{ICP27}$ cells were seeded into a 150 ml culture flask and cultured overnight. Cells were infected with 0.03 MOI (virus number/cell) oncolytic virus oHSV-BJR obtained from example 1, and incubated at 37° C. in a $CO_2$ incubator, until at least 90% of cells showed cytopathic expression. Cells in media were harvested. The cell mixture was the crude virus stock.

(3) Purification of the Oncolytic Virus oHSV-BJR

The crude stock of oncolytic virus oHSV-BJR underwent three times of freeze and thaw at −80° C./37° C. and clarified at 4° C. by low centrifugation, and the supernatant collected. The supernatant was filtered and concentrated by 0.6 μM hollow fiber, followed by ultra-filtration and concentration using 0.1 μM hollow fiber. Subsequently, the virus stock was further purified by heparin affinity chromatography. The pure virus was concentrated using an additional 0.1 μM hollow fiber.

(4) mRNA Expression Analysis

Cells were harvested, and RNA isolated by using Qiagen RNA purification kit. cDNA was synthesized with Thermofisher reverse transcription reagent. And ICP27 and ICP34.5 mRNA levels were analyzed by semi-quantitative PCR (20 cycles of PCR) using ICP27 or ICP34.5 specific primers. β-actin served as the loading control.

(5) Protein Expression Analysis

Cells were harvested, washed by 1×PBS, and collected by centrifugation. Proteins were isolated using RIPA buffer solution. Protein concentration was measured by BCA using BSA as standard to make the standard curve. Proteins were separated on a 4%-20% gradient SDS-PAGE gel and transferred to a PVDF membrane. The membrane was blocked by 5% powder milk prepared in 0.05% Tween 20-containing PBS, subsequently incubated with primary antibodies prepared in 2.5% powder milk-containing PBST at room temperature for 2 hrs. The immunoblot was washed by PBST for 3 times, and incubated with secondary antibodies prepared in a 2.5% powder milk-containing PBST at room temperature for 1 hr. The membrane was incubated with chemiluminescent substrates from Piece, and the protein bands were visualized using ChemiDoc (Bio-Rad). 8-actin was used as the loading control.

(6) miRNA Expression Analysis miRNA was isolated using Thermofisher pure miRNA isolation kit, RNA probes was labeled using the DIG RNA labeling kit from Roche, and miRNA analyzed by Northern blotting.

(7) Tumor Cell Culture

Cervical cancer cells Hela, cervical squamous cancer cells siHA breast cancer cells SK-BR3, and breast cancer cells ME-180 were all purchased from ATCC, USA. Hela, siHA and ME-180 were cultured in DMEM supplemented with 7.5% fatal bovine serum (FBS) and 1× penicillin/streptomycin. SK-BR3 was cultured in McCoy media supplemented with 7.5% FBS and 1× penicillin/streptomycin. Cells were passaged every three days for maintenance.

Example 3

Introduced miRNAs were Expressed from oHSV-BJ and Significantly Affected the Expression of the Targeted Gene In order to examine whether miRNAs are expressed from oncolytic virus oHSV-BJR in normal cells as expected and affect the expression of target viral genes, Vero cells were infected with 3 MOI oncolytic virus oHSV-BJR or wild-type virus KOS. Cells were harvested 1 day after infection, small RNAs and proteins were isolated. EGFP and ICP34.5 miRNA were assayed by Northern blot, respectively while HSV-1 ICP27 and ICP34.5 proteins were analyzed by Western blot using ICP27 and ICP34.5-specific antibodies.

Figure 4:
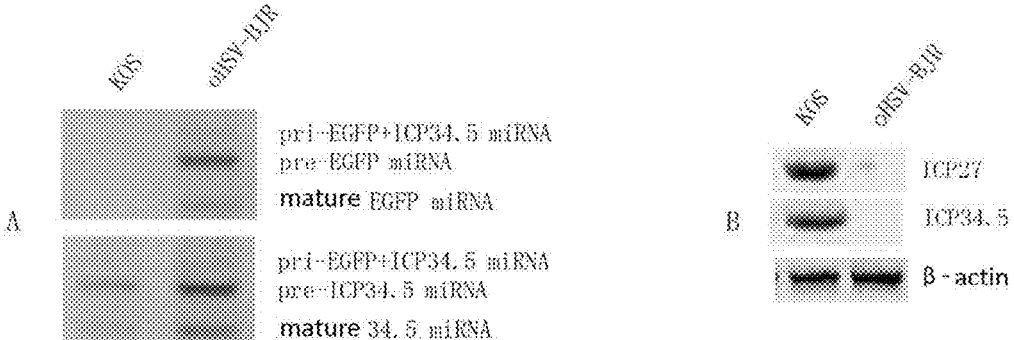
FIG. 4: Expression of EGFP and ICP34.5 miRNA from the oncolytic virus oHSV-BJR in normal cells and their inhibition of protein biosynthesis of target genes ICP27 and ICP34.5. Vero cells were infected with 0.25 MOI (virus/cell) HSV-1 wild-type virus KOS or the oncolytic virus oHSV-BJR. A portion of the cells were harvested after one day, and small RNAs were isolated and miRNAs detected by Northern blot (A). The remaining cells were collected after two days of infection, proteins isolated, and the levels of ICP27 and ICP34.5 proteins detected by Western blot (B).

No EGFP primary miRNA (pri-miRNA), EGFP precursor miRNA (pre-miRNA), and EGFP mature miRNA were detected in wild-type KOS-infected cells. However, ICP34.5-specific pri-miRNA, pre-miRNA, and mature miRNA were all expressed to an easily detectable level with more pre-miRNA and mature miRNA observed compared to pri-miRNA, a phenomenon which is consistent with literature reports that host cells encodes a miRNA against ICP34.5 to restrict HSV-1 replication. pri-miRNA, pre-miRNA, and mature miRNA of both EGFP and ICP34.5 were all expressed to a detectable level in oHSV-BJR infected cells with much more EGFP and ICP34.5 pre-miRNA and mature miRNA than pri-miRNA seen. Moreover, ICP34.5 pre-miRNA and mature miRNA levels in the oncolytic virus-infected cells were much higher than those seen in KOS-infected cells (FIG. 4A). Both ICP27 and ICP34.5 proteins were produced to an easily detectable level in KOS-infected cells. However those two proteins were below the detection limit in oHSV-BJR infected cells (FIG. 4B). Those results indicate that introduced EGFP and ICP34.5 miRNAs, were robustly expressed from oncolytic virus oHSV-BJR in normal cells and inhibit the expression of targeted viral genes significantly.

Example 4

Tumor cells possess a functional interfering RNA biosynthesis pathway; a trace amount of Drosha was produced while interfering RNA biosynthesis significantly was inhibited or completely abrogated in oncolytic virus oHSV-BJR-infected tumor cells. As a result, the targeted genes were robustly expressed in oncolytic virus oHSV-BJR-infected cells with expression levels similar to those seen in wild-type virus KOS infected cells.

In order to examine whether tumor cells have a functional small-interfering-RNA biosynthesis pathway, tumor Hela, siHA SK-BR3, or ME-180 cells were transfected with an ICP27-expressing plasmid or ICP27 with target sequence and miRNA co-expression plasmid, respectively. Cells were harvested two days after transfection, and proteins isolated. ICP27 protein was analyzed by Western blot using ICP27 specific antibody.

In order to determine whether the expression of Drosha siRNA and the inhibitory triplet repeats from oncolytic virus oHSV-BJR in tumor cells affect the expression of Drosha, inhibit or abrogate interfering RNA synthesis in the cells, and whether ICP27 and ICP34.5 can be robustly expressed from the oncolytic virus in tumor cells. Tumor Hela, siHA, SK-BR3, or ME-180 cells were infected with 0.5 MOI KOS or oncolytic virus oHSV-BJR, respectively. Cells were harvested 2 days after infection, and small RNAs and proteins were isolated.

The triplet repeats and Drosha siRNA as well as EGFP and ICP34.5 miRNAs were detected by Northern blot, while Drosha, ICP27 and ICP34.5 proteins were analyzed by Western blot.

Figure 5:
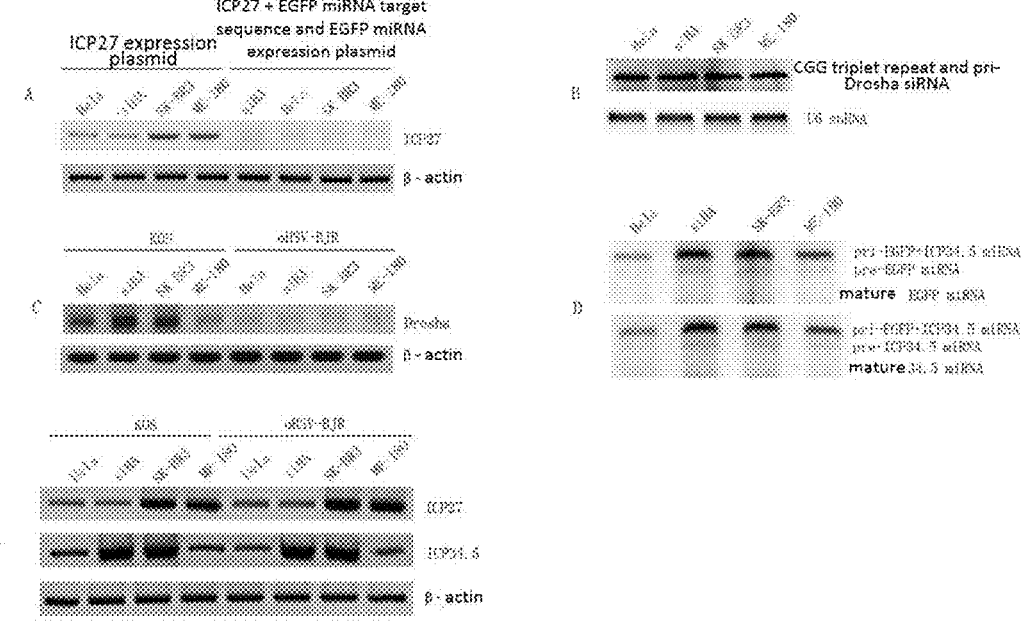
FIG. 5: A functional small-interfering-RNA biosynthesis pathway observed in tumor cells; significant decrease in Drosha expression and small interfering RNA biosynthesis, and robust expression of ICP27 and ICP34.5 seen in the oncolytic virus-infected tumor cells. In order to detect whether tumor cells possess a functional small-interfering-RNA biosynthesis pathway, cervical tumor Hela cells, cervical squamous cancer siHA cells, breast cancer SK-BR3 cells, and breast cancer ME-180 cells were transfected with an ICP27 expression plasmid or an ICP27+ target sequence and miRNA co-expression plasmid. Cells were collected after two days of transfection, proteins isolated, and protein of the essential gene ICP27 of HSV-1 detected by Western blot (A). In order to detect whether the expression of the inhibitory triplet repeats and Drosha siRNA from the oncolytic virus oHSV-BJR in cancer cells influences the expression of Drosha, whether the pathway for small interfering RNA biosynthesis is inhibited or abrogated in the oncolytic virus-infected cancer cells, and whether ICP27 and ICP34.5 can be robustly expressed from the oncolytic virus in cancer cells, cancer cells Hela, SiHA, SK-BR3, and ME-180 were infected with KOS or the oncolytic virus oHSV-BJR (0.5 MOI), respectively. Cells were collected after one day of infection, and small RNAs and proteins were isolated. The triplet repeats and Drosha siRNA (B) as well as EGFP and ICP34.5 miRNA (D) were detected by Northern blot, while Drosha (C), ICP27 and ICP34.5 (E) proteins were detected by Western blot.

Expression of EGFP miRNA inhibited the expression of ICP27 from ICP27 with target sequence and miRNA co-expression plasmid (FIG. 5A). Drosha pri-RNA and CGG triplet repeats were expressed to an easily detectable level (FIG. 5B) in all the four oncolytic virus-infected tumor cells, but the amounts of both Drosha pre-siRNA and mature siRNA were below the detection level (the results not shown). Drosha protein reached a detectable level in all the four tumor cells infected with wild-type virus KOS, but in all the four oncolytic virus-infected tumor cells, the Drosha protein level was very low (FIG. 5C). The EGFP and ICP34.5 pri-miRNA reached a detected level, while the levels of EGFP and ICP34.5 pre-miRNA and mature miRNA were all very low or could not be detected (FIG. 5D). Correspondingly, ICP27 and ICP34.5 proteins in oHSV-BJR-infected tumor cells were expressed to a level basically identical to that seen in the cells infected with KOS (FIG. 5E). The results showed that in oncolytic virus oHSV-BJR infected tumor cells, the interfering RNA synthesis pathway was inhibited or completely abrogated, and the target viral genes of oHSV-BJR could be robustly expressed with an efficiency similar to that observed with wild-type virus KOS.

Example 5

Figure 6:
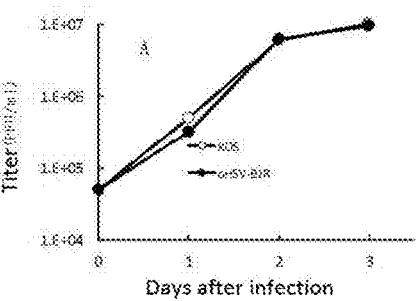
FIG. 6: Similar replication kinetics of oncolytic virus oHSV-BJR and the wild-type virus KOS observed in cancer cells. Various cancer cells were infected with 0.1 MOI KOS or oHSV-BJR. Cells in media were collected at different days after infection, and viruses remaining in the cells were released into the culture media through three cycles of freeze and thaw. Complementing cells were infected with the viruses, and viral titers determined through plaque assay (plaque forming unit/milliliter, PFU/ml). A: cervical tumor Hela cell; B: cervical squamous cancer siHA cell; C: breast cancer SK-BR3 cell; and D: breast cancer ME-180 cell.
Figure 6:
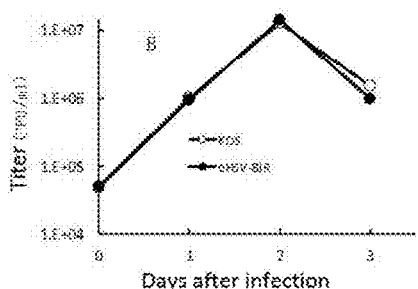
Figure 6:
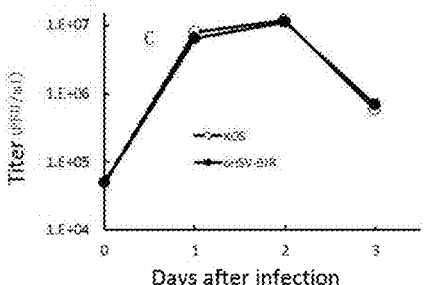
Figure 6:
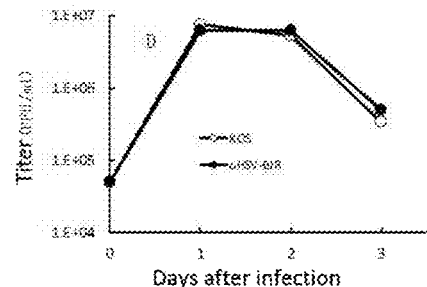

Oncolytic Virus oHSV-BJR Possesses a Replication Capacity Similar to that Seen with Wild-Type Virus KOS in Cancer Cells In order to understand the mechanism by which the oncolytic virus kills cancer cells, the replication ability of the virus in tumor cells was evaluated. 4 cancer cells including cervical tumor Hela cells, cervical squamous cancer siHA cells, breast cancer SK-BR3 cells, and breast cancer ME-180 cells were infected with 0.1 MOI KOS or oHSV-BJR, respectively. Cells in media were harvested at different days after infection. Viruses remaining in the cells were released into the media by three cycles of freeze and thaw at $-80/37°$ C. and virus stocks clarified by low-speed centrifugation. Complementing cells were infected with the viruses, and viral titers determined by plaque assay (plaque forming unit/milliliter, PFU/ml). Although the recombinant virus oHSV-BJR propagated at different rates in Hela (FIG. 6A), siHA (FIG. 6B), SK-BR3 (FIG. 6C), and ME-180 (FIG. 6D), the replication kinetics of the recombinant virus in each cell type was basically identical to that observed with KOS.

Example 6

Oncolytic Virus oHSV-BJR Like the Wild-Type Virus KOS Killed Tumor Cells Effectively.

In order to analyze the activity of oncolytic virus oHSV-BJR to kill tumor cells, tumor cervical Hela cells, cervical squamous cancer siHA cells, breast cancer SK-BR3 cells, or breast cancer ME-180 cells were infected with 0.25 or 0.5 MOI wild-type KOS or oHSV-BJR, respectively. Cell viability was analyzed at different days after infection and cell death rates calculated. More cells died with a MOI used for oncolytic virus infection increasing any day after infection for all the four tumor cells. Cell death rate was different from one cell type to another at a given day after oncolytic virus infection, but the overall killing profile of tumor cells by the oncolytic virus was similar or even identical to that seen in cells infected with KOS for a given cell type (Tables 2 through 5).

TABLE 2

A basically identical killing efficiency observed in both oHSV-BJR and KOS-infected Hela cells. (Cell death rate shown by %)

| MOI | time | oHSV-BJR | KOS |
|---|---|---|---|
| 0.25 | Day 1 | 45 ± 5 | 50 ± 3 |
| | Day 2 | 60 ± 4 | 65 ± 4 |
| | Day 3 | 70 ± 5 | 80 ± 3 |
| | Day 4 | 95 ± 2 | 100 |
| 0.5 | Day 1 | 50 ± 4 | 65 ± 2 |
| | Day 2 | 65 ± 3 | 75 ± 3 |
| | Day 3 | 80 ± 5 | 90 ± 3 |
| | Day 4 | 100 | 100 |

TABLE 3

No significant difference in cell killing seen between oncolytic and KOS infected siHA cells. (Cell death rate shown by %)

| MOI | time | oHSV-BJR | KOS |
|---|---|---|---|
| 0.25 | Day 1 | 88 ± 3 | 90 ± 5 |
| | Day 2 | 96 ± 2 | 100 |
| | Day 3 | 100 | 100 |
| 0.5 | Day 1 | 95 ± 2 | 95 ± 3 |
| | Day 2 | 99 ± 1 | 100 |
| | Day 3 | 100 | 100 |

TABLE 4

Similar cell-killing profiles seen in both oncolytic virus-infected and KOS infected SK-BR3 cells. (Cell death rate shown by %)

| MOI | time | oHSV-BJR | KOS |
|---|---|---|---|
| 0.25 | Day 1 | 88 ± 3 | 90 ± 3 |
| | Day 2 | 96 ± 2 | 100 |
| | Day 3 | 100 | 100 |
| 0.5 | Day 1 | 95 ± 2 | 95 ± 2 |
| | Day 2 | 99 ± 1 | 100 |
| | Day 3 | 100 | 100 |

TABLE 5

Almost identical killing efficiency observed in both oncolytic virus-infected and KOS infected ME-180 tumor cells. (Cell death rate shown by %)

| MOI | time | oHSV-BJR | KOS |
|---|---|---|---|
| 0.25 | Day 1 | 85 ± 3 | 95 ± 3 |
| | Day 2 | 100 | 100 |
| | Day 3 | 100 | 100 |
| 0.5 | Day 1 | 99 ± 4 | 95 ± 2 |
| | Day 2 | 100 | 100 |
| | Day 3 | 100 | 100 |

Example 7

Oncolytic Virus oHSV-BJR is Safe to Normal Cells.

In order to evaluate whether oncolytic virus is safe to normal cells, Vero cells or primary human corneal epidermal cells were infected with 2 MOI oncolytic virus oHSV-BJR (2 MOI) or 0.5 MOI KOS. Cell viability of oHSV-BJR infected and mock infected (untreated) cells was examined 3 days after infection, and the viability of the cells infected with the wild virus KOS was assayed 2 days after infection.

All Vero cells and primary human corneal epidermal cells died 2 days after KOS infection (Table 6). A marginal portion of Vero and primary human corneal epidermal cells died any day after oncolytic virus infection (Table 6), and the survival rate of the cells was still as high as 95%, which was basically identical to that observed in the untreated cells. Those results indicated oncolytic virus oHSV-BJR obtained in example 1 is relatively safe to normal cells.

TABLE 6

Killing of normal cells by KOS but not by oncolytic virus. (Cell survival rate shown in %)

| virus | oHSV-BJR | KOS | untreated |
|---|---|---|---|
| Vero cell | 92 ± 3 | 0 | 95 ± 5 |
| corneal epidermal cell | 95 ± 3 | 0 | 97 ± 3 |

Example 8

Oncolytic Virus oHSV-BJR Significantly Inhibited the Growth of Lung, Gastric Cancer, Liver, and Rectal Tumor in Animals.

In order to evaluate the effectiveness and the broad spectrum of oncolytic virus oHSV-BJR in tumor treatment, mouse tumor models for human lung, gastric, liver and colon tumors were established. In vitro cultured human non-small cell tumor A549, gastric tumor NCI-N87, and liver cancer SK-HEP-1 cells were subcutaneously injected into BALB/c (lung and gastric tumors) or NPG (liver tumor) mice. When the tumors grew to 800-1000 mm$^3$, the tumors were dissected, cut into 30 mm$^3$ pieces, and then implanted into mice. When the tumors grew to 40-120 mm$^3$, intratumoral injection of oncolytic virus oHSV-BJR was initiated.

The rectal tumor model was established by directly subcutaneous injection of cultured rectal adenocarcinoma HCT-8 cells into a BALB/c mouse. When the tumor grew to 40-120 mm$^3$, intratumoral injection of oncolytic virus oHSV-BJR got started.

Intratumoral injection of oncolytic virus oHSV-BJR was performed by multiple-point injection once every three days for a total of three times with $2 \times 10^7$ infectious units suspended in 40 μl PBS injected each time. Each group in each model included 8 animals and injection of 40 μl PBS served as a negative control. Tumor volume was measured twice a week after the first virus injection, and the study lasted for 25 to 32 days after the first virus injection depending on when animals in control group needed to be euthanized. A tumor growth curve of tumor volume over days after the first virus injection was made and the relative inhibition rate calculated by comparing the tumor volume in test group to the tumor volume in the control group.

Figure 7:
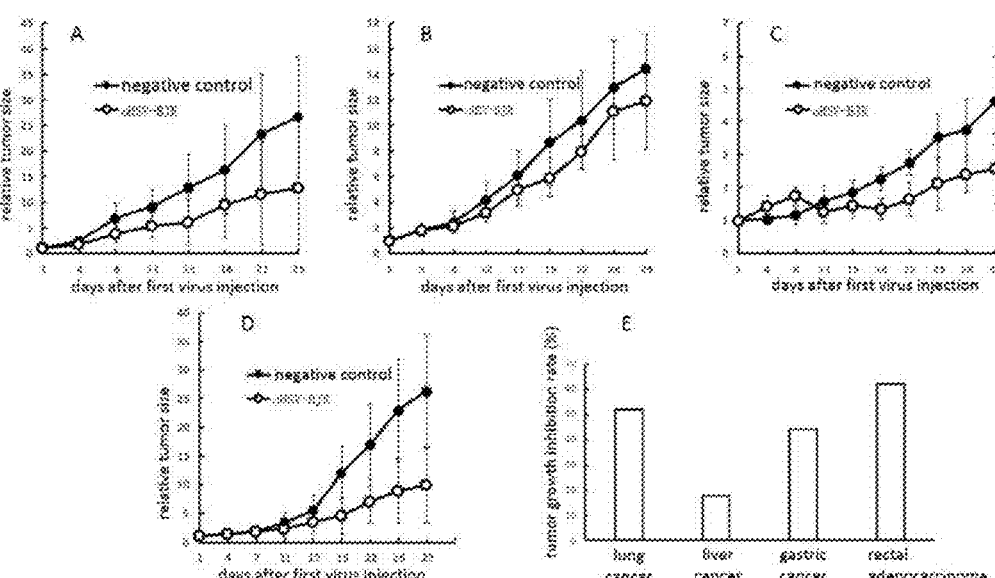
FIG. 7: Significant inhibition of tumor growth by oncolytic virus oHSV-BJR in animal tumor models. Cultured human non-small cell lung cancer A549 cells, gastric cancer NCI-N87 cells, and liver cancer SK-HEP-1 cells were subcutaneously injected into BALB/c (lung cancer and gastric cancer) or NPG (liver cancer) mice; At the day when the tumors grew to 1000 mm³, the tumors were dissected, cut into small pieces, and subcutaneously implanted into mice; when the tumors grew to 40-120 mm³, intratumoral injection of the virus began. A rectal cancer model was established by subcutaneous injection of rectal adenocarcinoma HCT-8 cells into BALB/c mice, and when the tumor grew to 40-120 mm³, intratumoral injection of the oncolytic virus got started. Intratumoral injection of the oncolytic virus was performed by multiple-point injection once every 3 days for a total of 3 times with a dose of $2 \times 10^7$ infectious units (suspended in 40 μl PBS) each time. PBS injection served as a negative control. After the first oncolytic virus injection, the tumor size was measured twice a week, and the study ended 25 to 32 days after the first virus injection depending on when animals needed to be euthanized in the negative control. A tumor growth curve was made based on the tumor size over the days after the first virus injection (A: lung cancer; B: liver cancer; C: gastric cancer; and D: rectal cancer), and a relative inhibition rate (E) was calculated by comparing the tumor sizes between test group and the negative control at the end of the study.

The tumor volume of animals in test group was smaller than that observed in the control group starting from the 8$^{th}$ day or so after the first virus injection (FIG. 7. A: lung tumor; B: liver tumor; C: gastric tumor and D: rectal tumor). The difference in tumor volumes between the virus-injected and control groups increased with the days after the first virus injection increasing. The inhibition rates of the oncolytic virus on the growth of lung, liver, gastric and rectal tumors at the end of study were 52.2, 19.5, 45.2, 64.6%, respectively.

In summary, the inventor believes the major issues of currently available oncolytic virus, i.e. low efficiency in tumor treatment for a given tumor type and a small suited patients' population for a given virus, are attributable to the caveats' associated with their design strategies: Selective replication of currently available oncolytic viruses in tumor cells is achieved at the expenses of viral replication.

Oncolytic viruses are currently designed mainly utilizing the following three strategies:

1) Oncolytic viruses are generated by deleting one or more nonessential viral genes, which are required for the viral replication in normal cells but not needed for the virus in tumor cells thus allowing for the virus to selectively replicate in tumor cells and eventually kill them. Normal cells encode multiple mechanisms to restrict viral infection while each virus encodes one or more gene products to antagonize the host' antiviral defense, thus allowing the virus to replicate in normal cells. Deletion of such viral gene(s) from the viral genome renders the virus mutants (oncolytic viruses) unable to propagate in normal cells while those mutants still maintains the ability to replicate in tumor cells because anti-viral functions are impaired in numerous tumor cells due to various reasons. In order to ensure the safety of an oncolytic virus to normal cells, more than one gene is needed to be deleted. But such a mutant virus generally replicates poorly in various tumor cells since only one anti-viral function or two are missing or impaired among multiple defensive mechanisms for any given tumor cell-type. Studies have demonstrated an oncolytic virus generated by this strategy replicates with a rate from several folds to one order of magnitude slower than that observed for wild-type virus in tumor cells in vitro, and the replication rate of such an oncolytic virus might be slower than wild-type virus by 1-3 orders of magnitude in tumors in animal. Also, clinical studies have shown that the therapeutic benefits of such an oncolytic virus are generally not satisfactory. A majority of currently available oncolytic viruses were generated using this strategy with or without minor modifications 2) Oncolytic viruses are generated by putting the expression of one or two viral essential genes under the control of a tumor-specific promoter. An oncolytic virus generated using this strategy is no doubt safe to normal cells since a tumor-specific promoter is not active in normal cells, thus resulting in no viral replication due to no regulated gene product produced. Oncolytic viruses of this kind have an advantage over the oncolytic viruses created using the first strategy, i.e. oncolytic viruses of this kind possess an intact genome. But such oncolytic viruses are inherently associated with a viral replication-related issue, i.e. disruption of a highly-coordinated order of viral gene expression. Viral genes are divided into several categories according to temporal order of gene expression after infection. Genes of each category are expressed with the expression lasting only for a short period of time, followed by the expression of the genes of the next category to ensure the temporal expression of viral genes. A tumor-specific promoter drives a continuous expression of the regulated viral gene(s) from an oncolytic viral genome in tumor cells, which definitely interferes with the timely initiation of expression of the gene(s) of the next class, thus resulting in impaired viral replication of the oncolytic virus in tumor cells. One can anticipate an oncolytic virus generated by this strategy should not replicate well in numerous tumor cells, and in vitro and in vivo studies have shown that is the case in vitro and in vivo. Up to now, a few of oncolytic viruses have been generated using this strategy.

3) Oncolytic viruses are generated by inserting a tissue-specific miRNA target sequence into the 3' UTR of a viral essential gene. A tissue-specific miRNA might be over-expressed in normal cells while no such a miRNA is produced or such production is highly impaired in tumor cells. Therefore, insertion of a miRNA target sequence into the 3' UTR of a viral essential gene could result in no or impaired production of the regulated viral gene product from the virus leading to no or severely impaired viral replication in normal cells while the virus can replicate in tumor cells. The following two issues might be intrinsically associated with an oncolytic virus developed using this strategy: 1) Such an oncolytic virus could be used only for treatment of a specific tumor type with a limited patient population; 2 the therapeutic benefits might be limited because for any given tumor type, miRNA production might be impaired but not abrogated, thus leading to a limited viral replication in tumor cells. Only a limited number of oncolytic viruses have been developed using this strategy.

Oncolytic viruses generated using above-mentioned strategies have been shown to be safe in clinic and each virus could be potentially used for treatment of various tumors. But currently available oncolytic viruses generally perform poorly. In order to overcome the weaknesses associated with currently available oncolytic viruses, and fulfill the potential of an oncolytic virus in treatment of tumors, we exploited a novel strategy as described in this disclosure to develop effective and broad-spectrum oncolytic viruses for tumor treatment. The basic concept of the strategy is to insert exogenous elements into a viral genome and utilize the inserted elements to regulate the protein production of one or more viral genes. The oncolytic viruses generated by this strategy maintain two essential features required for robust viral replication, which are generally absent from a majority of currently available oncolytic viruses: 1) intact viral genome with no single nucleotide deleted or replaced from the genome. This is critical for robust viral replication since each gene product, is directly or indirectly involved in or contributes to viral replication; 2) expression of viral genes in a temporally-coordinated manner. Viral genes are divided into several categories according to the order of gene expression after infection. Genes of each category are expressed with the expression lasting only for a short period of time, followed by the expression of the genes of the next category. Disruption of such an order, for example by utilizing a cellular or tumor-specific promoter to drive the expression of a viral gene, could result in severely impaired viral replication. For oncolytic viruses generated using our strategy, once the regulated genes are expressed, their expression is driven by their endogenous promoters, thus maintaining the temporal order of all the viral gene expression to ensure effective viral replication. The inserted sequences utilized for generation of the oncolytic viruses using our strategy basically include three elements: 1) interfering RNA target sequence inserted into the 5' or 3' UTR of one, two or more viral essential genes; 2) the first expression cassette, which expresses the first interfering RNA in the first cells; and 3) the second expression cassette, which specifically expresses inhibitory components in second cells that interferes with or abrogates interfering RNA biosynthesis pathway. In the first cells, the first interfering RNA, which can be either siRNA or miRNA, is constitutively expressed from the first expression cassette, thus targeting the interfering RNA target sequence located at the 5' or 3'UTR of the mRNA of the regulated viral gene leading to no protein or a trace amount of protein produced. As a result, the virus does not replicate in these cells or replicates poorly. In the second cells, a fusion promoter, which consists of a tumor-specific promoter fused with an enhancer, drives the expression of inhibitory components from the second expression cassette to both interfere with the biosynthesis and inhibit the activity of the enzyme(s) involved in interfering RNA biosynthesis pathway, thus resulting in no interfering RNA or a tracer amount of interfering RNA produced in those cells leading to robust expression of the regulated gene(s) and viral replication. In order to enhance the safety of the oncolytic viruses, in certain embodiments, more than one copy of the interfering RNA target sequence is inserted in the 5' or 3' UTR of one viral essential gene; in certain embodiments, the interfering RNA target sequence are inserted in the 5' or 3' UTR of more than one viral essential gene; or alternatively, in certain embodiments, a second interfering RNA, which targets the ORF of a non-essential viral gene is expressed from the first expression cassette when the first interfering RNA target sequence is inserted into the 5' or 3' UTR of one viral essential gene to ensure no viral replication in the first cells. To expand the clinic application of the oncolytic viruses, a fusion promoter consisting of a tumor-specific promoter being active in a variety of tumor cells and an enhancer is chosen to drive the expression of inhibitory components from the second expression cassette to both interfere with the biosynthesis and inhibit the activity of the enzyme(s) involved in interfering RNA biosynthesis pathway. A tumor-specific promoter dictates the expression of the inhibitory components specifically in tumor cells. A tumor-specific promoter being active in a variety of tumor cells such as hTERT promoter, which has been shown to be active in 85-90% of tumor cells tested, is chosen to ensure the inhibitory components can be expressed from the viruses in a majority of tumor cells. Addition of an enhancer to form a fusion promoter is to ensure the sufficient expression of the inhibitory components even in the tumor cells in which the activity of the tumor-specific promoter is low. Compared to all the strategies used for generating oncolytic viruses, ours as described in this disclosure is totally different and brand new. And the safety and efficacy of the oncolytic virus generated using this strategy have been demonstrated in vitro and in animals by exemplary embodiments.

The above-mentioned embodiments were executed to simply demonstrate the concepts and the idea provided in the present disclosure, which was not intended to identify key or essential features of the claimed subject matter, nor was it intended to limit the scope of the claimed subject matter. The present disclosure may be modified and changed in various ways known to a person skilled in the art. Modifications, substitutions, and combinations made based on the present disclosure shall all be covered in the scope of protection of the present disclosure.

INDUSTRIAL APPLICABILITY

The oncolytic virus provided in the present disclosure can selectively kill target cells (such as tumor cells) through selective replication, but does not affect non-target cells (such as normal cells). In particular, the oncolytic virus generated using the strategy provided in the present disclosure can be applied to cancer treatment.

What is claimed is:

1. An oncolytic virus, wherein the genome of the oncolytic virus contains the following exogenous elements:

(1) a first expression cassette comprising a first promoter, a first interfering RNA expression sequence for expressing a first interfering RNA, and a second interfering RNA expression sequence for expressing a second interfering RNA;

(2) a target sequence; and (3) a second expression cassette, wherein:

the nucleotide sequence of the target sequence is the sequence set forth in SEQ ID NO: 1, the nucleotide sequence of the first interfering RNA is the sequence set forth in SEQ ID NO: 2, and the nucleotide sequence of the second interfering RNA is the sequence set forth in SEQ ID NO: 3;

the first interfering RNA expression sequence is used to express the first interfering RNA which binds to the target sequence in a first cell, the first interfering RNA expression sequence being driven by the first promoter so as to express the first interfering RNA in the first cell;

the target sequence is located at the 5' or 3' untranslated region (UTR) of an essential gene required for replication of the oncolytic virus;

the second expression cassette comprises a second promoter and an inhibitory component expression sequence, wherein the inhibitory component expression sequence is used to express an inhibitory component which inhibits the biosynthesis and/or bioactivity of a first enzyme involved in the biosynthesis of interfering RNA, in a second cell, the inhibitory component expression sequence being driven by the second promoter so as to express the inhibitory component in the second cell, wherein the inhibitory component comprises a third interfering RNA which inhibits expression of a second enzyme involved in the biosynthesis of the first enzyme, wherein the nucleotide sequence of the third interfering RNA is the sequence set forth in SEQ ID NO:4; and the first and the second cells are different cell types.

2. The oncolytic virus of claim 1, wherein the second interfering RNA acts on the open reading frame (ORF) of a nonessential gene, which is not needed for the virus to replicate in vitro, so as to interfere with expression of the nonessential gene, and the second interfering RNA expression sequence is expressed under the control of the first promoter.

3. The oncolytic virus of claim 2, wherein the second cell is a tumor cell of a mammal, and the first cell is a non-tumor cells of the mammal.

4. The oncolytic virus of claim 1, wherein the target sequence is inserted into the 5' or 3' UTR of one or more essential genes of the oncolytic virus.

5. The oncolytic virus of claim 4, wherein the oncolytic virus is selected from the group consisting of herpes simplex virus, adenovirus, vaccinia virus, Newcastle disease virus, poliovirus, coxsackie virus, measles virus, mumps virus, vaccinia virus, vesicular stomatitis virus, and influenza virus.

6. The oncolytic virus of claim 2, wherein the oncolytic virus is herpes simplex virus, the nonessential gene is ICP34.5, and the target sequence is inserted into the 5' or 3' UTR of one or more essential gene of the oncolytic virus, wherein the one or more essential gene is ICP27.

7. The recombinant oncolytic virus of claim 2, wherein the first promoter is a constitutive promoter.

8. The oncolytic virus of claim 1, wherein the second promoter is a human tumor-specific promoter.

9. The oncolytic virus of claim 1, wherein the enzyme is Dicer, Drosha, or an Argonaute.

10. The oncolytic virus of claim 1, wherein the inhibitory component further comprises expanded nucleotide triplet repeats which inhibit the bioactivity of Drosha, or a non-coding RNA which inhibits Dicer activity.

11. The oncolytic virus of claim 8, wherein the second expression cassette further contains an enhancer sequence for enhancing expression of the inhibitory component expression sequence.

* * * * *

```
                            SEQUENCE LISTING

<160> NUMBER OF SEQ ID NOS: 8

<210> SEQ ID NO 1
<211> LENGTH: 22
<212> TYPE: DNA
<213> ORGANISM: Artificial sequence
<220> FEATURE:
<223> OTHER INFORMATION: The base sequence of the target sequence

<400> SEQUENCE: 1
caagctgacc ctgaagttca ta                                            22

<210> SEQ ID NO 2
<211> LENGTH: 21
<212> TYPE: RNA
<213> ORGANISM: Artificial sequence
<220> FEATURE:
<223> OTHER INFORMATION: The base sequence of the first interfering RNA

<400> SEQUENCE: 2
augaacuuca gggucagcuu g                                             21

<210> SEQ ID NO 3
<211> LENGTH: 22
<212> TYPE: RNA
<213> ORGANISM: Artificial sequence
<220> FEATURE:
<223> OTHER INFORMATION: The sequence of the second interfering RNA

<400> SEQUENCE: 3
cuugccuguc uaacucgcua gu                                            22

<210> SEQ ID NO 4
<211> LENGTH: 25
<212> TYPE: RNA
<213> ORGANISM: Artificial sequence
<220> FEATURE:
<223> OTHER INFORMATION: The base sequence of the third interfering RNA

<400> SEQUENCE: 4
cuugcugaau acuugguccu uggug                                         25

<210> SEQ ID NO 5
<211> LENGTH: 2679
<212> TYPE: DNA
<213> ORGANISM: Artificial sequence
<220> FEATURE:
<223> OTHER INFORMATION: The base sequence of the DNA fragment A
```

-continued

<400> SEQUENCE: 5

```
aaataactcg agctgcgggc gctgttgttc catcatcctg tcgggcatcg caatgcgatt      60
gtgttatatc gccgtggtgg ccggggtggt gctcgtggcg cttcactacg agcaggagat     120
ccagaggcgc ctgtttgatg tatgacgtca catccaggcc ggcggaaacc ggaacggcat     180
atgcaaactg gaaactgtcc tgtcttgggg cccacccacc cgacgcgtca tatgtaaatg     240
aaaatcgttc ccccgaggcc atgtgtagcc tggatcccaa cgaccccgcc catgggtccc     300
aattggccgt cccgttacca agaccaaccc agccagcgta tccacccccg cccgggtccc     360
cgcggaagcg gaacggtgta tgtgatatgc taattaaata catgccacgt acttatggtg     420
tctgattggt ccttgtctgt gccggaggtg gggcggggggc cccgcccggg gggcggaact     480
aggaggggtt tgggagagcc ggccccggca ccacgggtat aaggacatcc accacccggc     540
cggtggtggt gtgcagccgt gttccaacca cggtcgttga cattgattat tgactagtta     600
ttaatagtaa tcaattacgg ggtcattagt tcatagccca tatatggagt tccgcgttac     660
ataacttacg gtaaatggcc cgcctggctg accgcccaac gacccccgcc cattgacgtc     720
aataatgacg tatgttccca tagtaacgcc aataggggact ttccattgac gtcaatgggt     780
ggactattta cggtaaactg cccacttggc agtacatcaa gtgtatcata tgccaagtac     840
gccccctatt gacgtcaatg acggtaaatg gcccgcctgg cattatgccc agtacatgac     900
cttatgggac tttcctactt ggcagtacat ctacgtatta gtcatcgcta ttaccatggt     960
gatgcggttt tggcagtaca tcaatgggcg tggatagcgg tttgactcac ggggatttcc    1020
aagtctccac cccattgacg tcaatgggag tttgttttgg caccaaaatc aacgggactt    1080
tccaaaatgt cgtaacaact ccgccccatt gacgcaaatg ggcggtaggc gtgtacggtg    1140
ggaggtctat ataagcagag ctctctggct aactgccacc atggtgagca agggcgagga    1200
gctgttcacc ggggtggtgc ccatcctggt cgagctggac ggcgacgtaa acggccacaa    1260
gttcagcgtg tccggcgagg gcgagggcga tgccacctac ggcaagctga ccctgaagtt    1320
catctgcacc accggcaagc tgcccgtgcc ctggcccacc ctcgtgacca ccctgaccta    1380
cggcgtgcag tgcttcagcc gctacccga ccacatgaag cagcacgact tcttcaagtc    1440
cgccatgccc gaaggctacg tccaggagcg caccatcttc ttcaaggacg acggcaacta    1500
caagacccgc gccgaggtga agttcgaggg cgacaccctg gtgaaccgca tcgagctgaa    1560
gggcatcgac ttcaaggagg acggcaacat cctggggcac aagctggagt acaactacaa    1620
cagccacaac gtctatatca tggccgacaa gcagaagaac ggcatcaagg tgaacttcaa    1680
gatccgccac aacatcgagg acggcagcgt gcagctcgcc gaccactacc agcagaacac    1740
ccccatcggc gacggccccg tgctgctgcc cgacaaccac tacctgagca cccagtccgc    1800
cctgagcaaa gaccccaacg agaagcgcga tcacatggtc ctgctggagt tcgtgaccgc    1860
cgccgggatc actctcggca tggacgagct gtacaagtaa cgggcctcga ctgtgccttc    1920
tagttgccag ccatctgttg tttgcccctc ccccgtgcct tccttgaccc tggaaggtgc    1980
cactcccact gtccttttcct aataaaatga ggaaattgca tcgcattgtc tgagtaggtg    2040
tcattctatt ctggggggtg gggtggggca ggacagcaag ggggaggatt gggaagacaa    2100
tagcaggcat gctggggatg cggtgggctc tatggcttct gaggtacaat aaaaacaaaa    2160
catttcaaac aaatcgcccc acgtgttgtc cttctttgct catggccggc ggggcgtggg    2220
tcacggcaga tggcgggggt gggcccggcg tacggcctgg gtgggcggag ggaactaacc    2280
```

| caacgtataa atccgtcccc gctccaaggc cggtgtcata gtgcccttag gagcttcccg | 2340 |
| cccgggcgca tccccccttt tgcactatga cagcgacccc cctcaccaac ctgttcttac | 2400 |
| gggccccgga cataacccac gtggcccccc cttactgcct caacgccacc tggcaggccg | 2460 |
| aaacggccat gcacaccagc aaaacggact ccgcttgcgt ggccgtgcgg agttacctgg | 2520 |
| tccgcgcctc ctgtgagacc agcggcacaa tccactgctt tttctttgcg gtatacaagg | 2580 |
| acacccacca tacccctccg ctgattaccg agctccgcaa ctttgcggac ctggttaacc | 2640 |
| acccgccggt cctacgcgaa ctggtcgaag ctttttata | 2679 |

```
<210> SEQ ID NO 6
<211> LENGTH: 3338
<212> TYPE: DNA
<213> ORGANISM: Artificial sequence
<220> FEATURE:
<223> OTHER INFORMATION: The base sequence of the DNA fragment B

<400> SEQUENCE: 6
```

| cccaaactcg agctgcgggc gctgttgttc catcatcctg tcgggcatcg caatgcgatt | 60 |
| gtgttatatc gccgtggtgg ccggggtggt gctcgtggcg cttcactacg agcaggagat | 120 |
| ccagaggcgc ctgtttgatg tatgacgtca catccaggcc ggcggaaacc ggaacggcat | 180 |
| atgcaaactg gaaactgtcc tgtcttgggg cccacccacc cgacgcgtca tatgtaaatg | 240 |
| aaaatcgttc ccccgaggcc atgtgtagcc tggatcccaa cgaccccgcc catgggtccc | 300 |
| aattggccgt cccgttacca agaccaaccc agccagcgta tccaccccg cccgggtccc | 360 |
| cgcggaagcg gaacggtgta tgtgatatgc taattaaata catgccacgt acttatggtg | 420 |
| tctgattggt ccttgtctgt gccggaggtg gggcgggggc cccgcccggg gggcggaact | 480 |
| aggaggggtt tgggagagcc ggccccggca ccacgggtat aaggacatcc accacccggc | 540 |
| cggtggtggt gtgcagccgt gttccaacca cggtcacgct tcggtgcctc tccccgattc | 600 |
| gggcccggtc gcttgctacc ggtgcgccac caccagaggc catatccgac accccagccc | 660 |
| cgacggcagc cgacagcccg gtcatggcga ctgacattga tatgctaatt gacctcggcc | 720 |
| tggacctctc cgacagcgat ctggacgagg accccccga gccggcggag agccgccgcg | 780 |
| acgacctgga atcggacagc aacggggagt gttcctcgtc ggacgaggac atggaagacc | 840 |
| cccacggaga ggacggaccg gagccgatac tcgacgccgc tcgccggcg gtccgcccgt | 900 |
| ctcgtccaga agacccggc gtacccagca cccagacgcc tcgtccgacg gagcggcagg | 960 |
| gccccaacga tcctcaacca gcgcccaca gtgtgtggtc gcgcctcggg gcccggcgac | 1020 |
| cgtcttgctc ccccgagcgg cacggggca aggtggcccg cctccaaccc ccaccgacca | 1080 |
| aagcccagcc tgcccgcggc ggacgccgtg ggcgtcgcag gggtcggggt cgcggtggtc | 1140 |
| ccggggccgc cgatggtttg tcggaccccc gccggcgtgc ccccagaacc aatcgcaacc | 1200 |
| cggggggacc ccgcccgggg gcggggtgga cggacggccc cggcgccccc catggcgagg | 1260 |
| cgtggcgcgg aagtgagcag cccgacccac ccggaggccc gcggacacgg agcgtgcgcc | 1320 |
| aagcaccccc cccgctaatg acgctggcga ttgcccccc gcccgcggac ccccgcgccc | 1380 |
| cggcccccgga gcgaaaggcg cccgccgccg acaccatcga cgccaccacg cggttggtcc | 1440 |
| tgcgctccat ctccgagcgc gcggcggtcg accgcatcag cgagagcttc ggccgcagcg | 1500 |
| cacaggtcat gcacgacccc tttgggggc agccgtttcc cgccgcgaat agccctgggg | 1560 |
| ccccggtgct ggcgggccaa ggagggccct ttgacgccga accagacgg gtctcctggg | 1620 |
| aaaccttggt cgcccacggc ccgagcctct atcgcacttt tgccggcaat cctcgggccg | 1680 |

-continued

```
catcgaccgc caaggccatg cgcgactgcg tgctgcgcca agaaaatttc atcgaggcgc    1740
tggcctccgc cgacgagacg ctggcgtggt gcaagatgtg catccaccac aacctgccgc    1800 tgcgcccccca ggaccccatt atcgggacgg ccgcggcggt gctggataac ctcgccacgc    1860
gcctgcggcc ctttctccag tgctacctga aggcgcgagg cctgtgcggc ctggacgaac    1920
tgtgttcgcg gcggcgtctg gcggacatta aggacattgc atccttcgtg tttgtcattc    1980
tggccaggct cgccaaccgc gtcgagcgtg gcgtcgcgga gatcgactac gcgacccttg    2040
gtgtcggggt cggagagaag atgcatttct acctccccgg ggcctgcatg gcgggcctga    2100
tcgaaatcct agacacgcac cgccaggagt gttcgagtcg tgtctgcgag ttgacggcca    2160
gtcacatcgt cgcccccccg tacgtgcacg gcaaatattt ttattgcaac tccctgtttt    2220
aggatcgcaa gctgaccctg aagttcatag tccaagctga ccctgaagtt catacgtcca    2280
catgaagcag cacgacttct gaccacatga agcagcacga cttgatccag acatgataag    2340
atacattgat gagtttggac aaaccacaac tagaatgcag tgaaaaaaat gctttatttg    2400
tgaaatttgt gatgctattg ctttatttgt aaccattata agctgcaata aacaagttaa    2460
caacaacaat tgcattcatt ttatgtttca ggttcagggg gaggtgtggg aggttttta    2520 aagcaagtaa aacctctaca aatgtggtat ggctgattat gatcctgcaa gcctcgtcgt    2580
cctggccgga ccacgctatc tgtgcaaggt ccccggcccc ggacgcgcgc tccatgagca    2640
gagcgcccgc cgccgaggcg aagactcggg cggcgccctg cccgtcccac caggtcaaca    2700
ggcggtaacc ggcctcttca tcgggaatgc gcgcgacctt cagcatcgcc ggcatgtccc    2760
cctggcggac gggaagtatc cagctcgacc aagctgtttt aagcttgtac aataaaaaca    2820
aaacatttca aacaaatcgc cccacgtgtt gtccttcttt gctcatggcc ggcggggcgt    2880
gggtcacggc agatggcggg ggtgggcccg gcgtacggcc tgggtgggcg gagggaacta    2940
acccaacgta taaatccgtc cccgctccaa ggccggtgtc atagtgccct taggagcttc    3000
ccgcccgggc gcatcccccc ttttgcacta tgacagcgac cccctcacc aacctgttct    3060 tacgggcccc ggacataacc cacgtggccc cccttactg cctcaacgcc acctggcagg    3120
ccgaaacggc catgcacacc agcaaaacgg actccgcttg cgtggccgtg cggagttacc    3180
tggtccgcgc ctcctgtgag accagcggca caatccactg cttttctctt gcggtataca    3240
aggacaccca ccatacccct ccgctgatta ccgagctccg caactttgcg gacctggtta    3300
accacccgcc ggtcctacgc gaactgctcg aggggaaa                          3338
```

<210> SEQ ID NO 7
<211> LENGTH: 2622
<212> TYPE: DNA
<213> ORGANISM: Artificial sequence
<220> FEATURE:
<223> OTHER INFORMATION: The base sequence of the DNA fragment C

<400> SEQUENCE: 7

```
aataatataa gcttgttgac attgattatt gactagttat taatagtaat caattacggg     60
gtcattagtt catagcccat atatggagtt ccgcgttaca taacttacgg taaatggccc    120
gcctggctga ccgcccaacg acccccgccc attgacgtca ataatgacgt atgttcccat    180
agtaacgcca atagggactt tccattgacg tcaatgggtg gagtatttac ggtaaactgc    240
ccacttggca gtacatcaag tgtatcatat gccaagtacg cccccctattg acgtcaatga    300 cggtaaatgg cccgcctggc attatgccca gtacatgacc ttatgggact ttcctacttg    360
```

```
gcagtacatc tacgtattag tcatcgctat taccatggtg atgcggtttt ggcagtacat      420
caatgggcgt ggatagcggt ttgactcacg gggatttcca agtctccacc ccattgacgt      480
caatgggagt ttgtttttggc accaaaatca acgggacttt ccaaaatgtc gtaacaactc     540
cgccccattg acgcaaatgg gcggtaggcg tgtacggtgg gaggtctata taagcagagc      600
tcgtttagtg aaccgtcaga tcgcctggat gctgatgaac ttcagggtca gcttggtttt     660
ggccactgac tgaccaagct gactgaagtt catcaggctg gctcagcact gctatgttgc      720
ctgctcttac tggctggagt gaagaccagc aaaggccatt cctgctgatg aacttcaggg      780
tcagcttggt tttggccact gactgaccaa gctgactgaa gttcatcagg cctgctgagt      840
gacagcaccc ctttggagcc ccctccctta tatctaatgg aagattatgt gggcaacccg      900
gtggtagccg gggtggtaga gtttgacagg caagcatgtg cgtgcagagg cgagtagtgc      960
ttgcctgtct aactcgctag tctcggcgac tgtgccttct agttgccagc catctgttgt     1020
ttgcccctcc cccgtgcctt ccttgaccct ggaaggtgcc actcccactg tcctttccta    1080
ataaaatgag gaaattgcat cgcattgtct gagtaggtgt cattctattc tggggggtgg    1140
ggtggggcag gacagcaagg gggaggattg ggaagacaat agcaggcatg ctggggatgc    1200
ggtgggctct atgggatact tcccgtccgc caggggggaca tgccggcgat gctgaaggtc    1260
gcgcgcattc ccgatgaaga ggccggttac cgcctgttga cctggtggga cgggcagggc    1320
gccgcccgag tcttcgcctc ggcggcgggc gctctgctca tggagcgcgc gtccggggcc    1380
ggggaccttg cacagatagc gtggtccggc caggacgacg aggcttgcag gatcataatc    1440
agccatacca catttgtaga ggttttactt gctttaaaaa acctcccaca cctccccctg    1500
aacctgaaac ataaaatgaa tgcaattgtt gttgttaact tgtttattgc agcttataat    1560
ggttacaaat aaagcaatag catcacaaat ttcacaaata aagcattttt ttcactgcat    1620
tctagttgtg gtttgtccaa actcatcaat gtatcttatc aggatccccg ccgccgccgc    1680
cgccgccgcc gccgccgccg ccgccgccgc cgccgccgcc gccgccgccg ccgccgccgc    1740
cgccgccgcc gccgccgccg ccgccgccgc cgccgccgcc gccgccgccg ccgccgccgc    1800
cgccgccgcc gccgccgccg ccgccgccgc cgccgccgcc gccgccgccg ccgccgccgc    1860
cgccgccgcc gccgccgccg ccgccgccgc cgccgccgcc gccgccgccg ccgccgccgc    1920
cgccgccgcc gccgccgccg ccgccgccgc cgccgccgcc gccgccgtct agagtaaagg    1980
accaagtatt cagcaagttc gcttgctgaa tacttggtcc ttgctgccta gttcaaagtc    2040
gccgtccagg cgccgcgctg ttccgtttct tgctgcctca agatcctcca ggcgatctga    2100
cggttcacta aacgagctct gcttatatag gcctcccacc gtacacgcct accgcggggg    2160
tggccggggc cagggcttcc cacgtgcgca gcaggacgca gcgctgcctg aaactcgcgc    2220
cgcgaggaga gggcggggcc gcggaaagga aggggagggg ctgggagggc ccggaggggg    2280
ctgggccggg gacccgggag gggtcgggac ggggcgggt ccgcgcgag gaggcggagc      2340 tggaaggtga aggggcagga cgggtgcccg ggtccccagt ccctccgcca cgtggggagc    2400
gcggtcctgg gcgtctgtgc ccgcgaatcc actgggagcc cggcctggcc ccgacagcgc    2460
agctgctccg ggcggacccg ggggtctggg ccgcgcttcc ccgcccgcgc gccgctcgcg    2520
ctcccagggt gcaggacgc cagcgagggc cccagcggag agaggtcgaa tcggcctagg    2580
ctgtggggta acccgaggga ggggccataa gcttatatat aa                       2622
```

<210> SEQ ID NO 8
<211> LENGTH: 162

-continued

```
<212> TYPE: RNA
<213> ORGANISM: Artificial sequence
<220> FEATURE:
<223> OTHER INFORMATION: The base sequence of the adenovirus type 5 VA1
      RNA

<400> SEQUENCE: 8
agcgggcacu cuuccguggu cugguggaua aauucgcaag gguaucaugg cggacgaccg        60
ggguucgagc cccguauccg gccguccgcc gugauccaug cgguuaccgc ccgcgugucg       120
aacccaggug ugcgacguca gacaacgggg gagugcuccu uu                         162
```